US011135248B2

United States Patent
Zhang et al.

(10) Patent No.: US 11,135,248 B2
(45) Date of Patent: Oct. 5, 2021

(54) STEM CELLS FROM URINE AND METHODS FOR USING THE SAME

(71) Applicant: Wake Forest University Health Sciences, Winston-Salem, NC (US)

(72) Inventors: Yuanyuan Zhang, Winston-Salem, NC (US); Anthony Atala, Winston-Salem, NC (US)

(73) Assignee: WAKE FOREST UNIVERSITY HEALTH SCIENCES, Winston-Salem, NC (US)

( * ) Notice: Subject to any disclaimer, the term of this patent is extended or adjusted under 35 U.S.C. 154(b) by 705 days.

(21) Appl. No.: 15/829,488

(22) Filed: Dec. 1, 2017

(65) Prior Publication Data

US 2018/0117087 A1    May 3, 2018

Related U.S. Application Data

(60) Division of application No. 12/614,901, filed on Nov. 9, 2009, now abandoned, which is a continuation-in-part of application No. PCT/US2008/006438, filed on May 20, 2008.

(60) Provisional application No. 60/939,247, filed on May 21, 2007, provisional application No. 60/943,215, filed on Jun. 11, 2007, provisional application No. 61/120,224, filed on Dec. 5, 2008, provisional application No. 61/172,444, filed on Apr. 24, 2009.

(51) Int. Cl.
*C12N 5/071* (2010.01)
*A61K 35/22* (2015.01)
*C12N 5/0775* (2010.01)

(52) U.S. Cl.
CPC ............ *A61K 35/22* (2013.01); *C12N 5/0668* (2013.01); *C12N 5/0684* (2013.01)

(58) Field of Classification Search
None
See application file for complete search history.

(56) References Cited

U.S. PATENT DOCUMENTS

| | | | |
|---|---|---|---|
| 4,153,512 | A | 5/1979 | Messner et al. |
| 5,912,116 | A | 6/1999 | Caldwell |
| 6,008,008 | A | 12/1999 | James et al. |
| 6,171,344 | B1 | 1/2001 | Atala |
| 6,235,527 | B1 | 5/2001 | Rao et al. |
| 6,444,205 | B2 | 9/2002 | Dinsmore et al. |
| 6,548,299 | B1 | 4/2003 | Pykett et al. |
| 6,723,131 | B2 | 4/2004 | Muschler |
| 2002/0012953 | A1 | 1/2002 | Jauho et al. |
| 2004/0152190 | A1 | 8/2004 | Sumita |
| 2005/0106634 | A1 | 5/2005 | Pfrieger et al. |
| 2005/0265978 | A1 | 12/2005 | Chancellor et al. |
| 2006/0039593 | A1 | 2/2006 | Sammak et al. |
| 2006/0153816 | A1 | 7/2006 | Brown et al. |
| 2007/0202536 | A1 | 8/2007 | Yamanishi et al. |
| 2007/0254295 | A1 | 11/2007 | Harvey et al. |
| 2008/0213230 | A1 | 9/2008 | Phillips et al. |

FOREIGN PATENT DOCUMENTS

| | | |
|---|---|---|
| JP | 2005-261292 | 9/2005 |
| JP | 2007-202512 | 8/2007 |
| JP | 2007-284383 | 11/2007 |
| WO | WO 2004/010852 A2 | 2/2004 |
| WO | WO 2004/084950 A2 | 10/2004 |
| WO | 2005/021738 | 3/2005 |
| WO | WO 2006/026730 A2 | 3/2005 |
| WO | WO 2005/033268 A2 | 4/2005 |
| WO | WO 2005-047529 A1 | 5/2005 |
| WO | WO 2006/135103 A1 | 12/2006 |

OTHER PUBLICATIONS

Szpalski et al, Bone Tissue Engineering: Current Strategies and Techniques—Part I: Scaffolds, Tissue Engineering: Part B, 2012, pp. 246-257.*
Sagrinati et al, Isolation and Characterization of Multipotent Progenitor Cells from the Bowman's Capsule of Adult Human Kidneys, American Society of Nephrology, 2006, pp. 2443-2456.*
Potier et al, Hypoxia affects mesenchymal stromal cell osteogenic differentiation and angiogenic factor expression, Bone 40 (2007) 1078-1087.*
Shi et al, Bone formation by human postnatal bone marrow stromal stem cells is enhanced by telomerase expression, Nature Biotech, 2002, pp. 587-591.*
Lui and Ma, Polymeric Scaffolds for Bone Tissue Engineering, Annals of Biomedical Engineering, vol. 32, No. 3, Mar. 2004, pp. 477-486.*
Liuyun et al, Preparation and biological properties of a novel composite scaffold of nano-hydroxyapatite/chitosan/carboxymethyl cellulose for bone tissue engineering, Journal of Biomedical Science 2009, 16:65, pp. 1-10.*
Fehrer et al, Reduced oxygen tension attenuates differentiationcapacity of human mesenchymal stem cells and prolongs their lifespan, Aging Cell (2007) 6, pp. 745-757.*
Di Donna et al, Telomerase Can Extend the Proliferative Capacity of Human Myoblasts, but Does Not Lead to Their Immortalization, Molecular Cancer Research, 2003, pp. 643-653.*
Levenberg et al, Differentiation of human embryonic stem cells on three-dimensional polymer scaffolds, PNAS, 2003, pp. 12741-12746.*
Zhang et al, Tissue engineering of blood vessel, J. Cell. Mol. Med. vol. 11, No. 5, 2007 pp. 945-957.*
Peeters et al,Simultaneous measurement of calcium transients and motion in cultured heart cells, Am J Physiol 1987;253:H1400-H1410.*

(Continued)

*Primary Examiner* — Maria Marvich
(74) *Attorney, Agent, or Firm* — Myers Bigel, P.A.

(57) ABSTRACT

Provided herein are stem cells and methods for producing a culture of stem cells from urine. The stem cells may be differentiated into an osteogenic, chondrogenic, adipogenic, endothelial, neurogenic or myogenic lineage. Methods of use of the cells are provided, including methods of treating a subject in need of a cell based therapy.

18 Claims, 13 Drawing Sheets

(56) References Cited

OTHER PUBLICATIONS

Hoenig et al, Tissue-Engineered Blood Vessels Alternative to Autologous Grafts?, Arterioscler Thromb Vase Biol., 2005, pp. 1128-1134.*
Zhang et al. Urine derived cells are a potential source for urological tissue reconstruction. The Journal of Urology. Nov. 2008; 180: 2226-2233.
Bodin A et al. Tissue-engineered conduit using urine-derived stem cells seeded bacterial cellulose polymer in urinary reconstruction and diversion. Biomaterials. 2010; 31: 8889-8901.
Fischer UM et al. Pulmonary passage is a major obstacle for intravenous stel cell delivery: the pulmonary first-pass effect. Stem Cells and Development. 2009; 18(5): 683-691.
Zonta S et al. Which the most suitable and effective route of administration for mesenchymal stem cell-based immunomodulation therapy in experimental kidney transplantation: endovenous or arterial? Transplantation Proceedings. 2010; 42: 1336-1340.
https://urology.ucsf.edu/patient-care/children/additional/vesicoureteral-reflux.
Lin C-S and Lue TF. Stem cell therapy for stress urinary incontinence: a critical review. Stem Cells and Development. 2012; 21(6) 834-843.
Liu GH et al. Skeletal myogenic differentiation of urine-derived stem cells and angiogenesis using microbeads loaded with growth factors. Biomaterials. Jan. 2013; 34(4): 1311-1326.
Ouyang B et al. Human urine-derived stem cells alone or genetically-modified with FGF2 improve type 2 diabetic erectile dysfunction in a rat model. PLoS One. Mar. 2014:9(3) e92825.
Liu G et al. Chapter 2: Urine derived stem cells: biological characterization and the potential clinic application. Turksen Kursad (ed.), Stem Cells: Current Challenges and New Directions, Stem Cell Biology and Regenerative Medicine 33. Springer. 2013, pp. 19-28.
Shi Y et al. Chapter 31: Cell therapy and muscle regeneration: Skeletal myogenic differentiation of urine-derived stem cells for potential use in treatment of urinary incontinence. Regenerative Medicine and Tissue Engineering. InTech. 2013, 787-793.
Lin C-S. Advances in stem cell therapy for erectile dysfunction. Advances in Andrology. vol. 2014 (2014), Article ID 140618, 10 pages. Abstract only.
Ono Y et al. Isolation and culture of tubular epithelial progenitor cells from cells in urine samples of a canine model of ischemia/reperfusion, and their potential use for the treatment of renal failure. Report for Health and Labour Sciences Research Grants from 2005 to 2006, Mar. 2006, pp. 31-33. Translation of relevant portions.
Kucia M et al. A population of very small embryonic-like (VSEL) CXCR4+SSEA-1+Oct-4+ stem cells identified in adult bone marrow. Leukemia. 2006; 20: 857-869.
Lee CN et al. Human cord blood stem cell therapy for treatment of stress urinary incontinence. J Korean Med Sci. 2010; 25: 813-6.
Zhang D et al. Urine-derived stem cells: a novel and versatile progenitor source for cell-based therapy and regenerative medicine. Genes & Diseases. Jul. 2, 2014; 1: 8-17.
Wang H-J et al. Development of cellular therapy for the treatment of stress urinary incontinence. Int Urogynecol J. 2011; 22: 1075-1083.
Gräs S and Lose G. The clinical relevance of cell-based therapy for the treatment of stress urinary incontinence. Nordic Federation of Societies of Obstetrics and Gynecology. Acta Obstetricia et Gynecologica Scandinavica. 2011; 90: 815-824.
Staack A and Rodriguez LV. Stem cells for the treatment of urinary incontinence. Curr Urol Rep. 2011; 12: 41-46.
Carr LK et al. Autologous muscle derived cell therapy for stress urinary incontinence: a prospective, dose ranging study. The Journal of Urology. Feb. 2013; 180: 595-601.
Liu G et al. Correction of diabetic erectile dysfunction with adipose derived stem cells modified with the vascular endothelial growth factor gene in a rodent diabetic model. PLOS One. Aug. 2013; 8(8): e72790, 13 pp.
Mitterberger M et al. Myoblast and fibroblast therapy for post-prostatectomy urinary incontinence: 1-year followup of 63 patients. The Journal of Urology. Jan. 2008; 179: 226-231.
Yang B et al. Myogenic differentiation of mesenchymal stem cells for muscle regeneration in urinary tract. Chin Med J. 2013; 126(15): 2952-2959.
Chen W et al. Skeletal myogenic differentiation of human urine-derived cells as a potential source for skeletal muscle regeneration. J Tissue Eng Regen Med. 2014; DOI: 10.1002/term.1914.
Fossum M et al. Isolation and in vitro cultivation of human urothelial cells from bladder washings of adult patients and children. Scandinavian Journal of Plastic and Reconstructive Surgery and Hand Surgery. 2003; 37(1): 41-45.
Fossum M et al. Long-term culture of human urothelial cells—a qualitative analysis. Scandinavian Journal of Plastic and Reconstructive Surgery and Hand Surgery. 2005; 18(1): 11-22.
Bharadwaj S et al. Characterization of urine-derived stem cells obtained from upper urinary tract for use in cell-based urological tissue engineering. Tissue Engineering: Part A. 2011; 17(15-16): 2123-2132.
Wu S et al. Human urine-derived stem cells seeded in a modified 3D porous small intestinal submucosa scaffold for urethral tissue engineering. Biomaterials. 2011; 32: 1317-1326.
Lang R et al. Self-renewal and differentiation capacity of urine-derived stem cells after urine preservation for 24 hours. PLOS One. Jan. 2013; 8(1): e53980, 11 pages.
Liu G et al. Skeletal myogenic differentiation of urine-derived stem cells and angiogenesis using microbeads loaded with growth factors. Biomaterials (2012), http://dx.doi.org/10.1016/j.biomaterials.2012.10.038.
Bharadwaj S et al. Multipotential differentiation of human urine-derived stem cells: potential for therapeutic applications in urology. Stem Cells. 2013; 31: 1840-1856.
Liu G et al. The effect of urine-derived stem cells expressing VEGF loaded in collagen hydrogels on myogenesis and innervation following after subcutaneous implantation in nude mice. Biomaterials (2013), http://dx.doi.org/10.1016/j.biomaterials.2013.07.077.
Endoscope: Medline Plus Medical Encyclopedia. U.S. National Library of Medicine NIH National Institutes of Health. Retrieved from Internet Dec. 14, 2012, 2 pp.
Lee JY et al. The effects of periurethral muscle-derived stem cell injection on leak point pressure in a rat model of stress urinary incontinence. Int Urogynecol J. 2003; 14: 31-37.
Strasser H et al. Autologous myoblasts and fibroblasts versus collagen for treatment of stress urinary incontinence in women: a randomised controlled trial. Lancet. 2007; 369: 2179-86.
Oliver PD and Ledouarin NM. Avian thymic accessory cells. The Journal of Immunology. Apr. 1984; 132(4);1748-1755.
Wang T et al. Cell-to-cell contact induces mesenchymal stem cell to differentiate into cardiomyocyte and smooth muscle cell. International Journal of Cardiology. 2006; 109: 74-81.
De Filippo RE and Atala A. Minimally invasive endoscopic treatment of vesicoureteral reflux and urinary incontinence. Pediatric Endosurgery & Innovative Techniques. 2000; 4(3): 179-188.
Kerr LA. Bulking agents in the treatment of stress urinary incontinence: history, outcomes, patient populations, and reimbursement profile. Reviews in Urology. 2005; 7 Suppl. 1: S3-S11.
Freshney "Cell Separation", *Culture of Animal Cells: A Manual of Basic Technique 5th Ed.* pp. 241-250 (2005).
Wu et al. "Implantation of Autologous Urine Derived Stem Cells Expressing Vascular Endothelial Growth Factor for Potential Use in Genitourinary Reconstruction", *The Journal Of Urology* 186:640-647 (2011).
Becker et al. "Stem Cells for Regeneration of Urological Structures", European Urology, Elsevier BV, NL, vol. 51, No. 5, Mar. 23, 2007, pp. 1217-1228, XP005934664.
Zhang et al. "A Novel Cell Source for Urologic Tissue Reconstruction", Journal of Urology; AUA Annual Meeting 2007; Anaheim, CA, USA; May 21, 2007; Lippincott Williams & Wilkins, Baltimore, MD, US, vol. 177 No. 4, Supplement p. 238, Apr. 2007, XP008129230.

(56) References Cited

OTHER PUBLICATIONS

Felix JS et al. Human epithelial cells cultured from urine: growth properties and keratin staining. In Vitro. Oct. 1980; 16(10): 866-874 Abstract only.

Fernandez-Conde M et al. Bone metaplasia of urothelial mucosa: an unusual biological phenomenon causing kidney stones. Bone. Mar. 1996; 18(3): 289-291.

Dörrenhaus A et al. Cultures of exfoliated epithelial cells from different locations of the human urinary tract and the renal tubular system. Arch Toxicol. 2000; 74: 618-626.

Zhang YY et al. Expansion and long-term culture of differentiated normal rate urothelial cells in vitro. In Vitro Cell Dev Biol. Jul./Aug. 2001; 37: 419-429.

Inoue CN et al. Reconstruction of tubular structures in three-dimensional collagen gel culture using proximal tubular epithelial cells voided in human urine. In Vitro Cell Dev Biol. Sep./Oct. Sep.-Oct. 2003; 39(8-9): 365-367.

Kitamura S et al. Establishment and characterization of renal progenitor like cells from S3 segment of nephron in rat adult kidney. The FASEB Journal. Nov. 2005; 19: 1789-1797.

Staack A et al. Molecular, cellular and developmental biology of urothelium as a basis of bladder regeneration. Differentiation. 2005; 73: 121-133.

Atala A et al. Tissue-engineered autologous bladders for patients needing cystoplasty. The Lancet. Apr. 15, 2006; 367: 1241-46.

Chung SY. Bladder tissue-engineering: a new practical solution? The Lancet. Apr. 15, 2006; 367: 1215-16.

Sagrinati C et al. Isolation and characterization of multipotent progenitor cells from the Bowman's Capsule of adult human kidneys. Journal of the American Society of Nephrology. 2006; 17: 2443-2456.

Glomerulus dictionary definition. Your Dictionary. 1 page. http://www.yourdictionary.com/glomerulus.

Forostyak O et al. CNS regenerative medicine and stem cells. Opera Med Physiol. 2016; 2(1): 55-62.

* cited by examiner

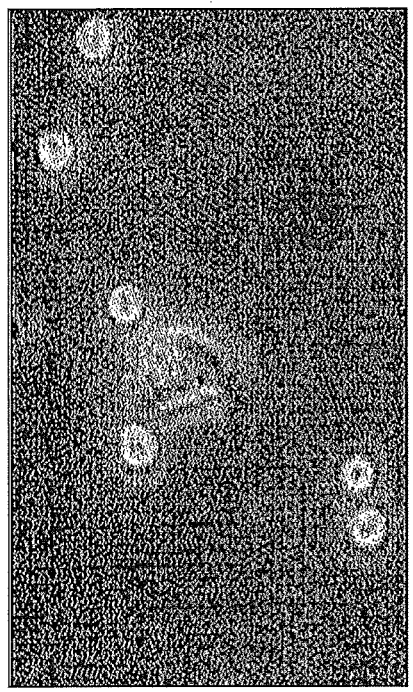# 
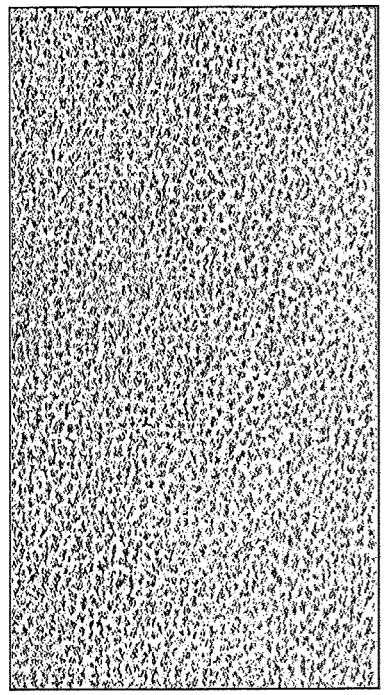
DAY 2
CELL CLONE
X400
DAY 5
DAY 10
FIG. 1

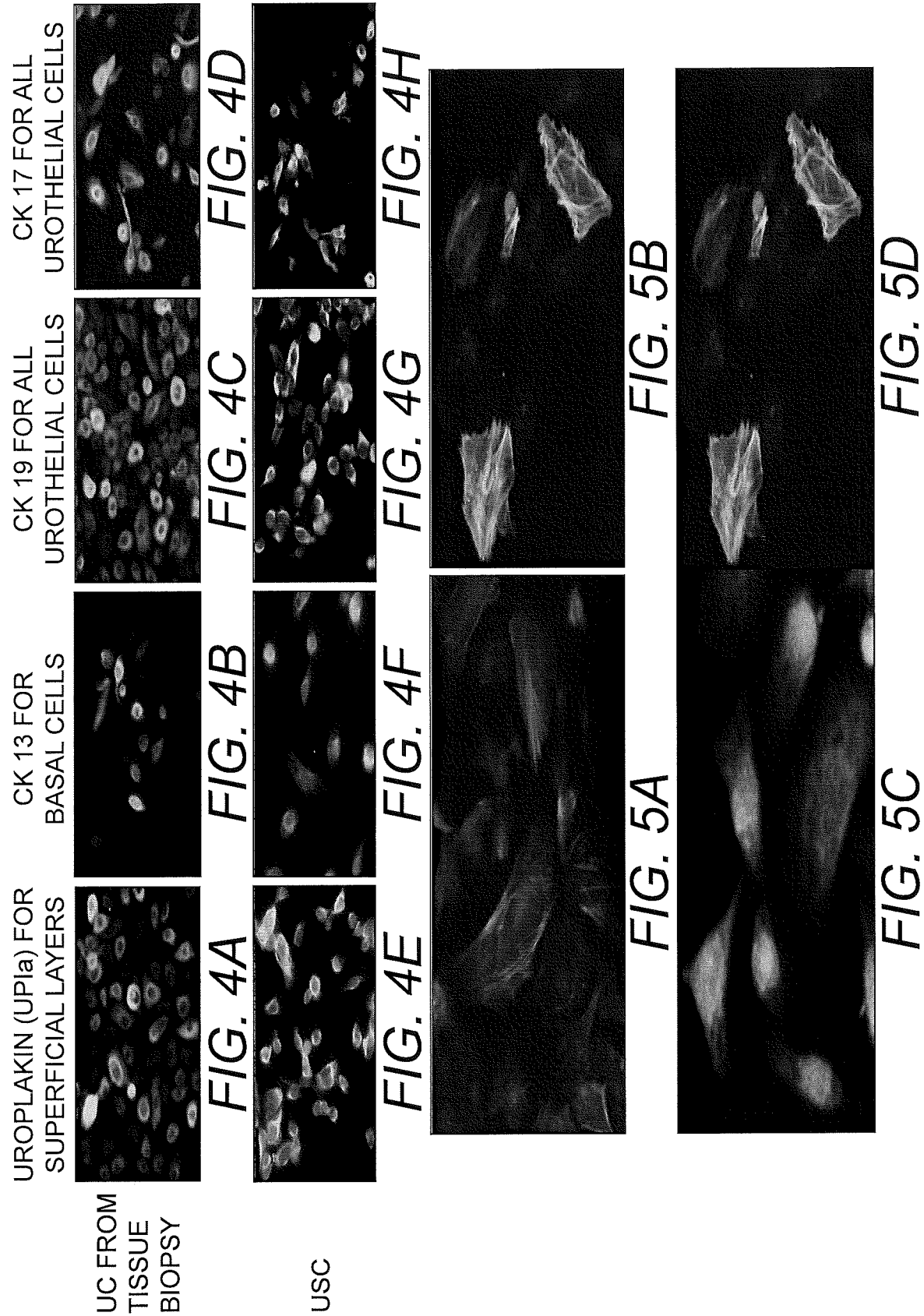

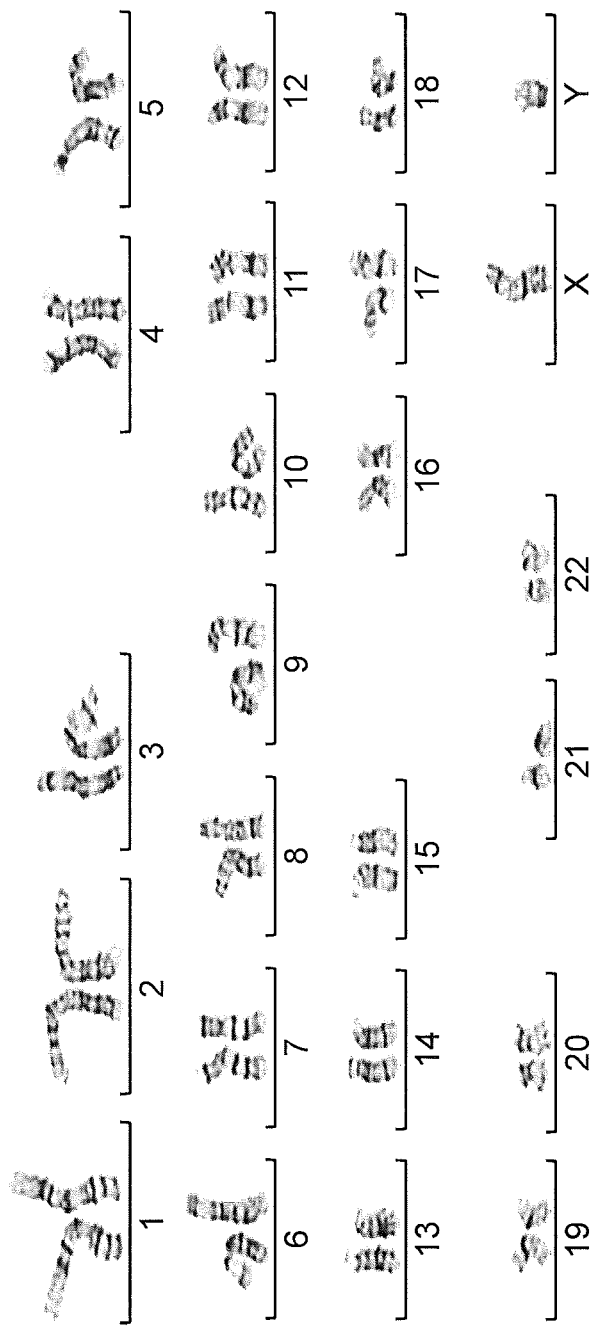
FIG. 9
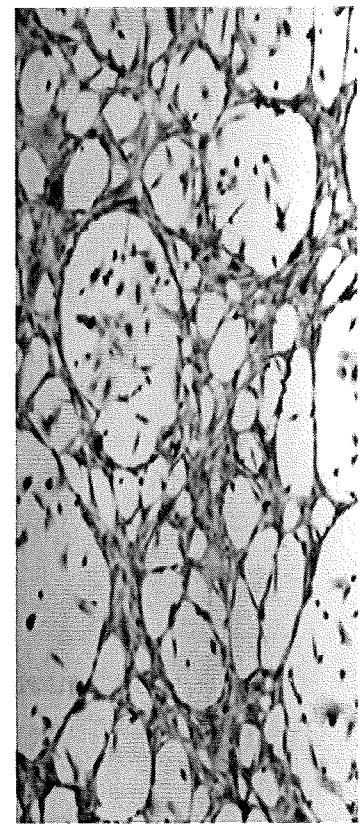
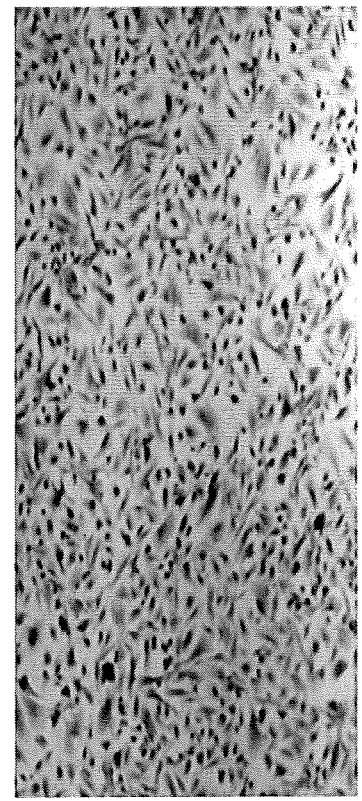
FIG. 10

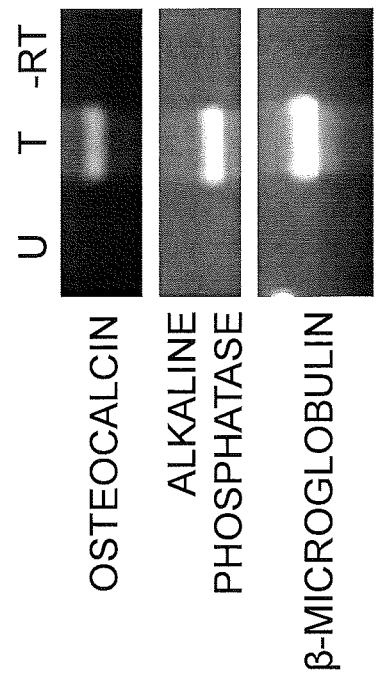
FIG. 12
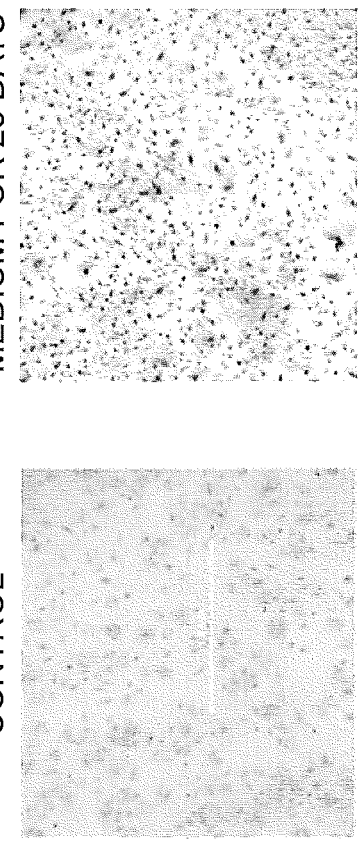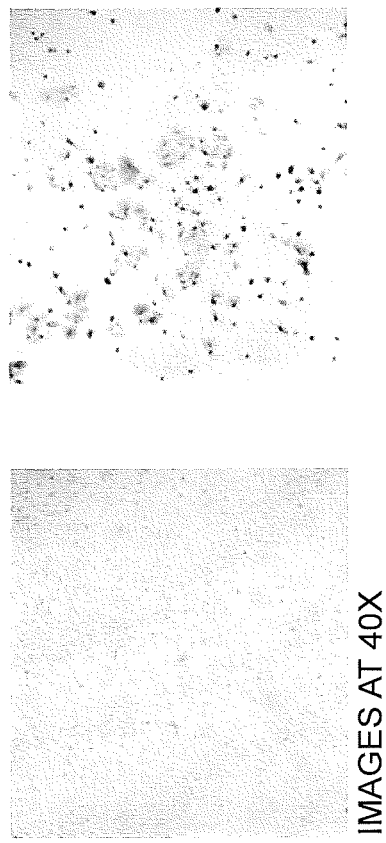
FIG. 11

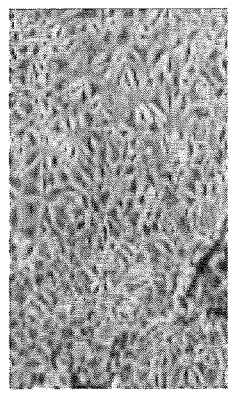
FIG. 13A
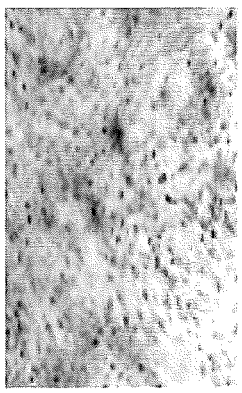
FIG. 13B
FIG. 13C
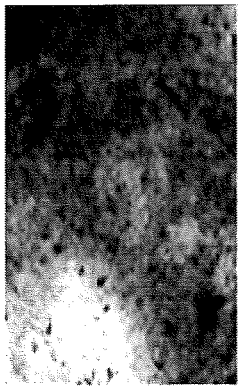
FIG. 13D
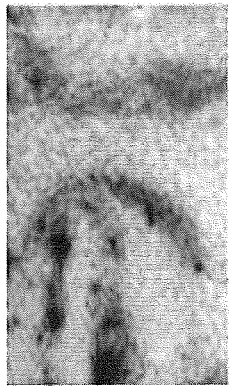
FIG. 13E
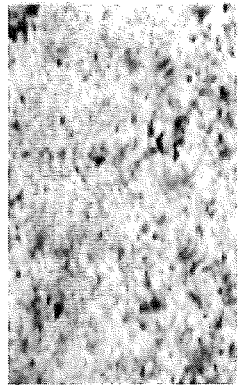
FIG. 13F
FIG. 13G
FIG. 13H
FIG. 13I

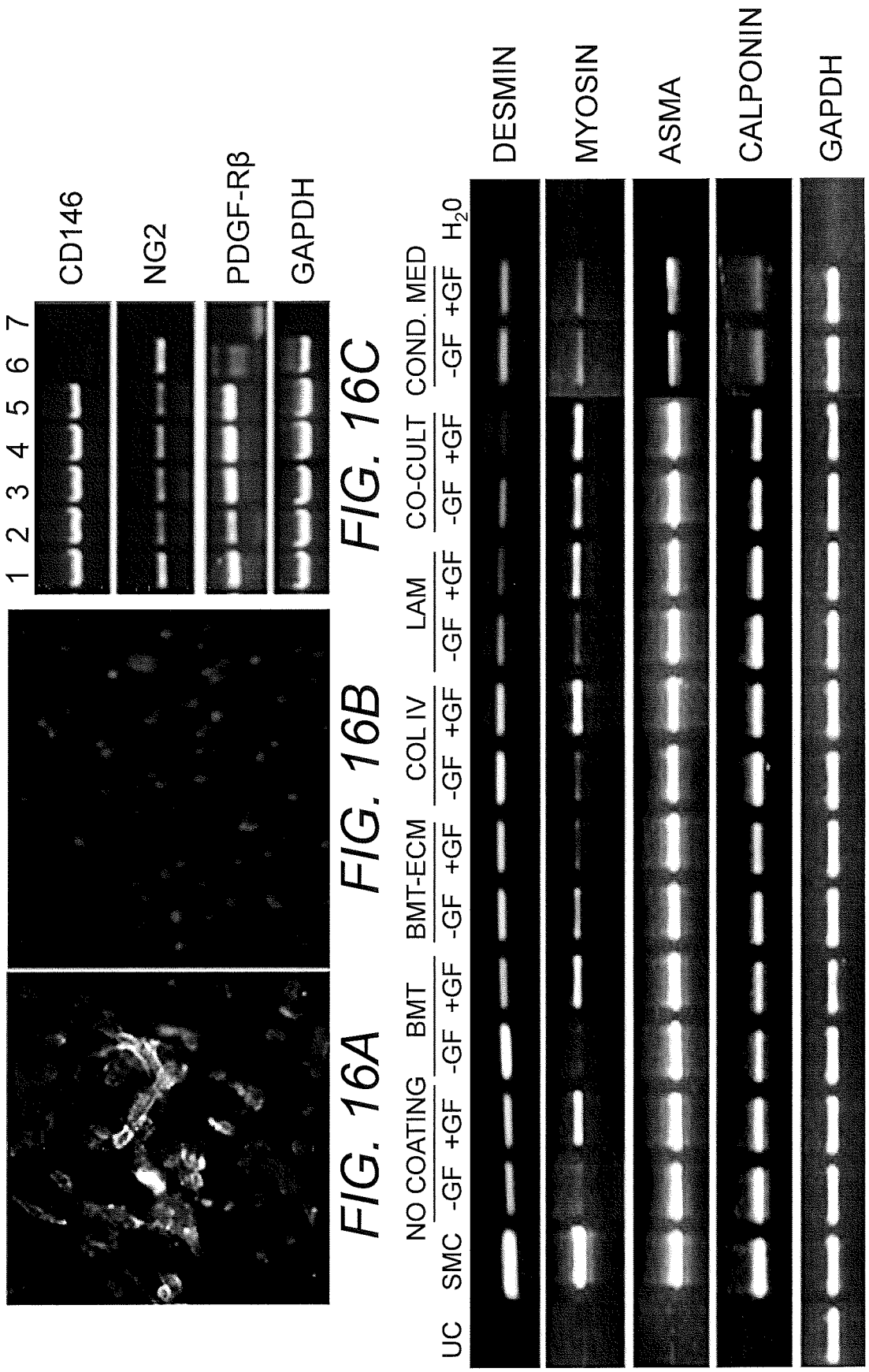

STEM CELLS FROM URINE AND METHODS FOR USING THE SAME

RELATED APPLICATIONS

This application is a divisional of and claims priority to U.S. patent application Ser. No. 12/614,901, filed Nov. 9, 2009, now pending, which claims priority to under 35 U.S.C. § 120, and is a continuation-in-part of, PCT application no. PCT/US2008/006438, filed May 20, 2008, which claims the benefit under 35 U.S.C. § 119(e) of U.S. Provisional Patent Application Ser. No. 60/939,247, filed May 21, 2007, and U.S. Provisional Patent Application Ser. No. 60/943,215, filed Jun. 11, 2007, the disclosure of each of which is incorporated herein by reference in its entirety.

This application also claims the benefit under 35 U.S.C. § 119(e) of U.S. Provisional Patent Application Ser. No. 61/120,224, filed Dec. 5, 2008, and U.S. Provisional Patent Application Ser. No. 61/172,444, filed Apr. 24, 2009, the disclosure of each of which is incorporated herein by reference in its entirety.

FIELD OF THE INVENTION

This invention relates generally to the isolation of stem cells from urine, cells isolated, differentiation thereof into multiple lineages, and methods of use of the same.

BACKGROUND OF THE INVENTION

Regenerative medicine is an applied field of tissue engineering that focuses on the regeneration of damaged tissues of the body. Applications of regenerative medicine include the reconstruction or replacement of organs and other tissues. However, a donor shortage limits the supply of viable cells to use for these applications. More alternative sources of cells are needed.

SUMMARY OF THE INVENTION

Provided herein are methods for producing a culture of differentiated cells, including: 1) providing urine stem cells (e.g., mammalian cells or human cells) isolated from a urine sample; and then 2) differentiating the urine stem cells, wherein said differentiating is osteogenic, chondrogenic, adipogenic, endothelial, neurogenic or myogenic; to produce said culture of differentiated cells.

In some embodiments, the differentiating is osteogenic, and the culture of differentiated cells express osteocalcin, Runx2, alkaline phosphatase, or a combination thereof. In some embodiments, the culture of differentiated cells comprise mineralized bone. In some embodiments, the culture of differentiated cells comprise calcium (i.e., show calcium deposition).

In some embodiments, the differentiating is adipogenic, and the culture of differentiated cells express the transcription factor PPARγ, lipoprotein lipase (LpL), or a combination thereof.

In some embodiments, the differentiating is chondrogenic, and the culture of differentiated cells express Sox9, collagen II, aggrecan, or a combination thereof.

In some embodiments, the differentiating is myogenic, and the culture of differentiated cells express actin, desmin, calponin, myosin, or a combination thereof.

In some embodiments, the differentiating is endothelial, and the culture of differentiated cells express vWF, CD 31, or a combination thereof.

In some embodiments, the differentiating is neurogenic, and the culture of differentiated cells express nestin.

An isolated differentiated cell produced by any of these methods is also provided.

Further provided is an isolated urine stem cell that is c-kit positive and can differentiate into two or more lineages selected from the group consisting of: bone, cartilage, fat, endothelium, nerve and muscle. In some embodiments, the cell is positive for a marker selected from: CD133, SSEA-A, CD90, CD73, CD105, pericyte CD146 (MCAM), NG2, PDGF-Receptorβ (PDGF-Rβ), and combinations thereof. In some embodiments, the cell is negative for a marker selected from CD31, CD34, CD45, and combinations thereof. In some embodiments, the cell expresses telomerase.

In some embodiments, the cell has undergone hypoxia preconditioning by culturing in a 1-2% $O_2$ environment.

Methods of providing a seeded tissue scaffold are further disclosed, including the steps of: providing an isolated urine stem cell as described herein; differentiating said urine stem cell, wherein said differentiating is osteogenic, chondrogenic, adipogenic, endothelial, neurogenic or myogenic, to produce differentiated cells; and seeding said differentiated cells onto a biocompatible tissue scaffold. In some embodiments, the tissue scaffold includes a collagen matrix. In some embodiments, the tissue scaffold includes a synthetic polymer (e.g., polyglycolic acid (PGA), polylactic acid (PLA) or polylactic-co-glycolic acid (PLGA)). In some embodiments, the tissue scaffold comprises a cellulose polymer.

A seeded tissue scaffold including a biocompatible tissue scaffold and urine stem cells (differentiated or undifferentiated) is also provided. In some embodiments, the tissue scaffold includes a collagen matrix. In some embodiments, the tissue scaffold includes a synthetic polymer (e.g., polyglycolic acid (PGA), polylactic acid (PLA) (e.g., poly L-lactide (PLLA), polylactic-co-glycolic acid (PLGA)). In some embodiments, the tissue scaffold comprises a cellulose polymer.

Further provided are methods of treating a subject in need thereof, including the steps of: providing a tissue substrate that includes urine stem cells; differentiating the urine stem cells, wherein the differentiating is osteogenic, chondrogenic, adipogenic, endothelial, neurogenic or myogenic, to produce differentiated cells; seeding the differentiated cells onto a biocompatible substrate; and transplanting said substrate into the patient.

Another aspect of the present invention is cultured tissue produced by a process as described herein. In some embodiments, the cultured tissue is suturable. In some embodiments, the cultured tissue is smooth muscle tissue characterized by a contractile response to calcium ionophor in vitro. In some embodiments, the smooth muscle tissue contracts upon administration of a contraction agonist four weeks after of in vivo implantation.

Also provided are methods of treating stress urinary incontinence (UI) or vesicoureteral reflux (VCR) in a subject in need thereof, comprising administering urine stem cells to said subject in a treatment effective amount. In some embodiments, administering is carried out by subcutaneous administration. In some embodiments, administering is carried out by endoscopic injection. In some embodiments, urine stem cells are tranfected with a nucleic acid encoding VEFG. In some embodiments, the methods further comprise administering endothelial cells. In some embodiments, the cells are provided in a pharmaceutically acceptable carrier, e.g., a collagen gel, a hydrogel, a temperature sensitive gel or a hyaluronic acid gel.

A further aspect of the present invention is the use of cells as described above for the preparation of a medicament for carrying out a method of treatment as described above.

The foregoing and other objects and aspects of the present invention are explained in greater detail in the drawings herein and the specification set forth below.

BRIEF DESCRIPTION OF THE DRAWINGS

FIG. 1. Microscopy images of stem cells from urine that have been cultured in vitro. The cells can proliferate without feeding layer cells.

FIG. 4A-FIG. 4H. Microscopy images of immunofluorescence staining with uroplakin (UPIa), cytokeratin 7, 13, 19, 17 and nucleic acid in human urothelium obtained from bladder biopsy (FIG. 4A-FIG. 4D) and USC (FIG. 4E-FIG. 4H).

FIG. 5A-FIG. 5D. Microscopy images of USC double stained for nucleic acids and markers specific to smooth muscle. The images show that urine-derived smooth muscle stem cells express smooth muscle protein markers such as alpha-smooth muscle actin (ASMA) (FIG. 5A), Calponin (FIG. 5B), Desmin (FIG. 5C) and Myosin (FIG. 5D).

FIG. 6A. Masson Trichrome staining and detection of USC grown on SIS scaffolds. FIG. 6B. LacZ-labeled USC identified on SIS matrix. FIG. 6C. Hematoxylin & Eosin (H&E) stained sections of urine cell-seeded BSM grafts. FIG. 6D. Human X/Y chromosomes of USC were noted within the BSM matrix.

FIG. 9. Giemsa band karyogram of clonal USC shows normal chromosome patterns on passage 6.

FIG. 10. Morphological changes of induced USC. Left Panel Non-induced USC as control, Right Panel Osteogenic differentiation of USC for 28 days.

FIG. 11. Histochemical staining for alkaline phosphatase and Alizarin Red S staining in USC differentiated in osteogenic media for 28 days.

FIG. 12. RT-PCR profile of bone-specific markers on osteogenic induced UPC.

FIG. 13A-FIG. 13I. Multilineage potential of cloned USC Cells cultured in induction media and assessed for differentiation typical of mesenchymal stem cells. (FIG. 13A) Adipogenic day 21: Oil Red O stain for lipid droplets. (FIG. 13B, FIG. 13C) Chondrogenic day 21: Alcian Blue staining for GAGs, Toluidine Blue for induced USC growth on laminin coated dishes+TGF-β3. (FIG. 13D-FIG. 13F) Osteogenic day 21: FIG. 13D) von Kossa staining for bone minerals; FIG. 13E) Alizarin Red staining for calcium deposition; FIG. 13F) Alkaline phosphatase. (FIG. 13G-FIG. 13I) RT-PCR of transcripts from FIG. 13G) adipogenic; FIG. 13H) osteogenic; FIG. 13I) chondrogenic differentiation. FIG. 13G, FIG. 13H—Lane 1: non-induced; Lane 2: induced: Lane 3: no RNA control. FIG. 13I—Lane 1: induced bone marrow stromal cells (positive control), lane 2: non-induced USC, lane 3: induced USC, lane 4: no RNA.

FIG. 16A-FIG. 16C. MSC/pericyte marker expression. Immunofluorescent staining of a USC clone at passage 3 (p3) by (FIG. 16A) CD146 monoclonal antibody and (FIG. 16B) negative isotype control. Secondary antibody was labeled with FITC. Nuclei stained with propidium iodide (PI). (FIG. 16C) RT-PCR for indicated marker genes. GAPDH is positive control. Lanes 1-5: USC (including 3 donors, p2-7), 6: RNA from freshly voided urine and lane 7: water control.

FIG. 17. RT-PCR performed on USC (p3) treated in the absence and presence of growth factors (TGF-β at 2.5 ng/ml and PDGF-BB at 5 ng/ml) and matrices for 14 days using smooth muscle-specific markers.

DETAILED DESCRIPTION OF THE PREFERRED EMBODIMENTS

Figure 2:
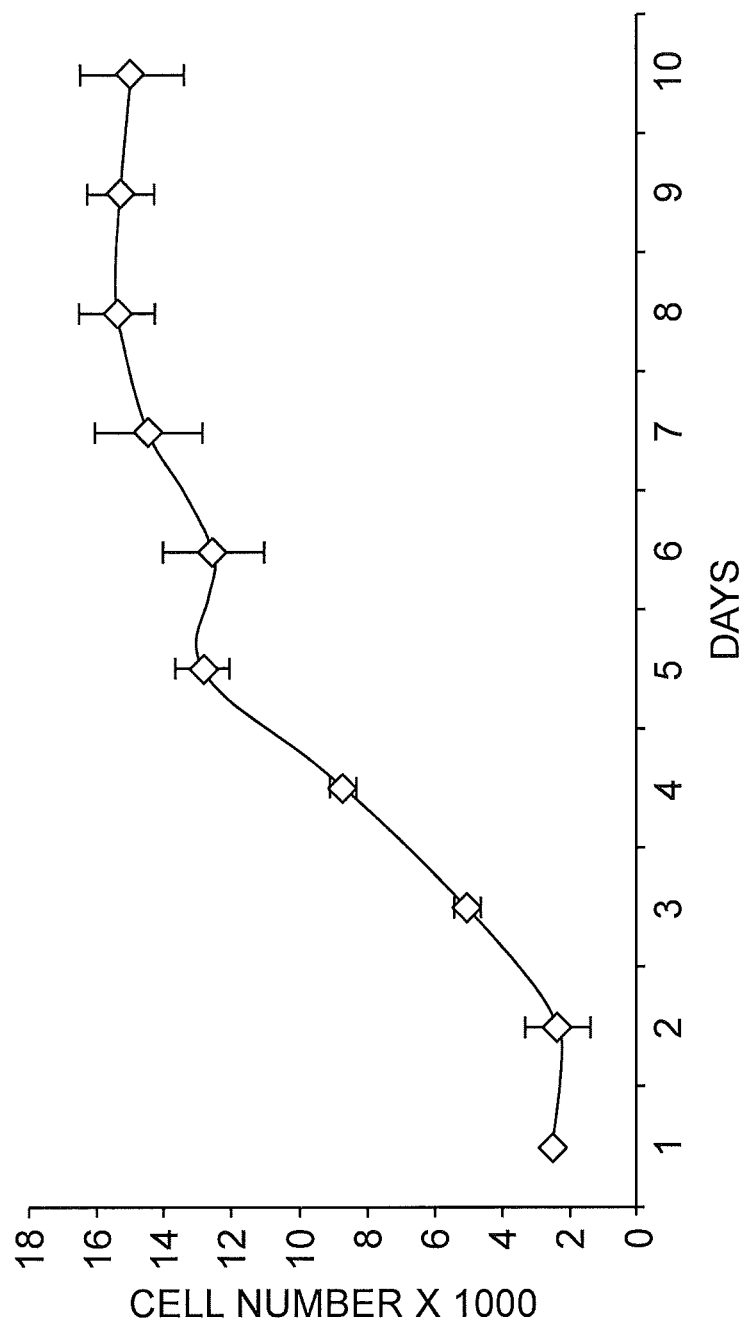
FIG. 2. Cell growth curve of urine cell cultures. Cells grew from a single cell to confluence in a 6-cm culture dish in 10 to 12 days.

The present invention concerns stem cells and methods of selecting and culturing multipotent stem cells from urine. Advantageously, cells found in urine may be obtained without the need for a tissue biopsy, preventing discomfort and possible complications associated with the harvest of cells.

The disclosures of all cited United States Patent references are hereby incorporated by reference to the extent that they are consistent with the disclosures herein. As used herein in the description of the invention and the appended claims, the singular forms "a," "an" and "the" are intended to include the plural forms as well, unless the context clearly indicates otherwise. Furthermore, the terms "about" and "approximately" as used herein when referring to a measurable value such as an amount of a compound, dose, time, temperature, and the like, is meant to encompass variations of 20%, 10%, 5%, 1%, 0.5%, or even 0.1% of the specified amount. Also, as used herein, "and/or" and "/" refer to and encompass any and all possible combinations of one or more of the associated listed items, as well as the lack of combinations when interpreted in the alternative ("or").

"Urine stem cells" or "USC" are cells normally found in, and collected and/or isolated from, urine, which cells as disclosed herein possess both pluripotency and proliferative potential. A USC is "pluripotent" in that it is capable of giving rise to various cell types within one or more lineages. For example, USC according to some embodiments possess the potential to differentiate into one or more of the following: bladder urothelial, smooth muscle, endothelium, interstitial cells, and even bone, muscle, epithelial cells and other types of cells and tissues (e.g., fat, cartilage, nerve). A previous report has indicated that urothelial cells may be able to differentiate into mature chondrocytes (Fernandez-Conde, *Bone* (1996) 18(3):289-91).

USC used to carry out the present invention are preferably mammalian cells, including primate muscle cells, including but not limited to human, pig, goat, horse, mouse, rat, monkey, baboon, etc. USC of other species, including birds, fish, reptiles, and amphibians, may also be used, if so desired.

The cells sloughed from the urinary tract lumen are generally believed to be old or damaged superficial cells that are difficult to culture and maintain in vitro. A few cells obtained from urine may grow rapidly on feeding layer cells. However, feeding layer cells are usually derived from embryonic mouse tissues that might transfer viruses from animal to human when human cells are cultured with the mouse feeder cells. To avoid this complication, according to some embodiments the UPCs disclosed herein can be grown without feeding layer cells. The UPCs possess mesenchymal stem cell features and show proliferative capability and pluripotency potential.

Without wishing to be bound by theory, our studies indicate that there are mixed cell populations in urine: stem cells and mature cells as well. As disclosed herein, urine contains urothelial stem cells and smooth muscle stem cells, as well as endothelial and interstitial stem cells. Stem cells that are found in urine may originate from bladder tissue, renal tissue, etc. In some embodiments, USC undergo selection against cells of renal origin. This can be accomplished by, for example, passaging the collected cells, as it is thought that renal cells generally do not survive passaging. In some embodiments USC will double upon growing between 24-48 hours (e.g., every 31.3 hours), allowing them to be grown in large quantities. In further embodiments, USC do not induce tumor formation (as compared to embryonic stem cells), and in some embodiments USC do not require feeder cells for growth or differentiation.

"Isolated" signifies that the cells are placed into conditions other than their natural environment. However, the term "isolated" does not preclude the later use of these cells thereafter in combinations or mixtures with other cells.

"Subjects" are generally human subjects and include, but are not limited to, "patients." The subjects may be male or female and may be of any race or ethnicity, including, but not limited to, Caucasian, African-American, African, Asian, Hispanic, Indian, etc. The subjects may be of any age, including newborn, neonate, infant, child, adolescent, adult, and geriatric. In some embodiments, subjects are from 0-5 years old, from 6-15 years old, from 16-25 years old, from 26-45 years old, and/or from 46-65 years old.

Subjects may also include animal subjects, particularly mammalian subjects such as canines, felines, bovines, caprines, equines, ovines, porcines, rodents (e.g., rats and mice), lagomorphs, primates (including non-human primates), etc., for, e.g., veterinary medicine and/or pharmaceutical drug development purposes.

1. Collection of Cells.

Urine stem cells may be collected from any animal that produces urine, including humans. In some embodiments of the present invention, urine stem cells are collected from the urine of a mammal. For example, USC may be collected from the urine of a dog, cat, pig, cow, horse, monkey or human. In particular embodiments, urine stem cells are obtained from the urine of a human.

Urine stem cells may be collected from any portion of the urinary tract. In some embodiments, USC are collected from the upper urinary tract (UUT) (kidneys, ureter), e.g., via a catheter such as a nephrostomy catheter. In other embodiments, USC are collected from the lower urinary tract (bladder, urethra), via a catheter such as a urinary catheter.

In some embodiments, USC are collected from samples of fresh spontaneous urine, or drainage urine through a urethral catheter or from a bladder wash. Urine samples can be centrifuged at 1500 RPM for 5 minutes at 4° C., the supernatant aspirated and cells washed with a suitable solution such as phosphate-buffered saline (PBS). The PBS may optionally contain 5% fetal bovine serum (FBS) and 1% penicillin-streptomycin to protect cells from injury and potential infection, respectively.

Further examples of methods and apparatuses for isolating cells from biological fluids may be found in, e.g., U.S. Pat. No. 5,912,116; U.S. Patent Application No. 20040087017; U.S. Patent Application No. 20020012953; and WO 2005/047529.

Generally speaking, we have found three types of cells in urine: 1) fully-differentiated urothelial cells, which are approximately 99% of the cells; 2) various differentiating cells (e.g., endothelial-like cells, epithelial-like cells, stromal-like cells, interstitial-like cells), which are approximately 0.1-0.2% of the cells, and 3) urine stem cells as described herein, which are approximately 0.2-0.7% of the cells.

2. Selection and Propagation of Cells.

In some embodiments, collected USC are expanded. "Expanding" refers to an increase in number of viable cells. Expanding may be accomplished by, e.g., growing the cells through one or more cell cycles wherein at least a portion of the cells divide to produce additional cells.

The "primary culture" is the first culture to become established after seeding collected cells into a culture vessel. "Passaging" refers to the transfer or subculture of a culture to a second culture vessel, usually implying mechanical or enzymatic disaggregation, reseeding, and often division into two or more daughter cultures, depending upon the rate of proliferation. If the population is selected for a particular genotype or phenotype, the culture becomes a "cell strain" upon subculture, i.e., the culture is homogeneous and possesses desirable characteristics. The establishment of "cell lines," as opposed to cell strains, are by and large undifferentiated, though they may be committed to a particular lineage.

USC according to some embodiments may be passaged from 0, 1 or 2 to 5, 6, 7, 8, 9, 10, 11 or 12 times. In some embodiments, one USC clone can generate $10^6$ cells in 3-4 weeks. According to some embodiments, $10^9$ cells may be generated from 3 or 4 urine samples in 6-7 weeks.

"Selection" can be based upon any unique properties that distinguish one cell type from another, e.g., density, size, unique markers, unique metabolic pathways, nutritional requirements, protein expression, protein excretion, etc. For example, cells may be selected based on density and size with the use of centrifugal gradients. Unique markers may be selected with fluorescent-activated cell sorting (FACS), immunomagnetic bead sorting, magnetic activated cell sorting (MACS), panning, etc. Unique metabolic pathways and nutritional requirements may be exploited by varying the makeup and/or quantity of nutritional ingredients of the medium on which cells are grown, particularly in a serum-free environment. Protein expression and/or excretion may be detected with various assays, e.g., ELISA.

In some embodiments, USC are selected by providing cells isolated from urine in a particular growing environment that promotes the growth of stem cells, such as stem cell medium. In some embodiments, the stem cell medium contains ¾ DMEM, ¼ Ham's F12, 10% FBS, 0.4 mg/ml hydrocortisone, $10^{-10}$ M, Chron Toxin, 5 mg/ml, insulin, 1.2 mg/ml adenine, 2.5 mg/ml transferrin plus 0.136 mg/ml 3,39,5-triiodo-L-thyronine, 10 mg/ml EGF, and 1% penicillin-streptomycin (Zhang et al., In vitro Cell Dev. Biol.-Animal 37:419, 2001). In further embodiments, isolated USC are provided in a particular growing environment that promotes the selective differentiation of the stem cells. For example, in some embodiments USC grown in keratinocyte serum free medium develop into urothelium. In further embodiments, USC grown in DMEM with 10% fetal bovine serum develop into smooth muscle-like cells. In some embodiments, endothelial-like cells may be cultured in M199 with 20% FBS, 2 mmol/l L-glutamine, EGF (5 nl/ml) 1% sodium pyruvate and 1% penicillin-streptomycin. In some embodiments, interstitial-like cells may be cultured in DMEM with 10% FBS, 2 mmol/l L-glutamine, and 1% penicillin-streptomycin.

In other embodiments, USC are selected by morphology. For example, cells isolated from urine may be diluted to a concentration allowing for the isolation of single cells (e.g., cells can be diluted to a concentration of approximately 0.5 cells/well in a multi-well plate), and observed under a microscope. Wells containing single cells can be retained for expansion, and selected by observed morphology, e.g., urothelium, smooth muscle, endothelium and/or interstitial cells.

Urine stem cells according to some embodiments of the present invention can be identified, selected, and/or isolated based on one or more "markers." Such markers include specific gene expression, antigenic molecules found on the surface of such cells, etc. In particular embodiments, urine stem cells are selected and isolated based upon the expression of at least one specific maker. In some embodiments, USC have one or more of the following markers such as CD117 (C-kit), SSEA-4, CD105, CD73, CD90, CD133, and CD44, and do not have an appreciable amount of one or more of the following markers: CD31, CD34, and CD45. Accordingly, certain embodiments embrace selecting and isolating urine stem cells which express one or more of CD117, SSEA-4, CD105, CD73, CD90, CD133, and CD44 and/or lack expression of one or more of CD31, CD34, and CD45. For example, in some embodiments a urine stem cell of the present invention is identified, selected, and/or isolated based on the expression of CD117. Urine stem cells according to some embodiments also express MSC/pericyte markers such as CD146 (MCAM), NG2 (a related antigen), and/or PDGF-Receptorβ (PDGF-Rβ). Marker expression may be probed by methods known in the art, e.g., western blot, RT-PCR, immunofluorescence, FACS, etc. In some embodiments, USC are positive for a marker selected from: CD133, SSEA-A, CD90, CD73, CD105, pericyte CD146 (MCAM), NG2, PDGF-Receptorβ (PDGF-Rβ), and combinations thereof, and wherein said cell is negative for a marker selected from CD31, CD34, CD45, and combinations thereof.

In some embodiments USC can be obtained as disclosed herein by collecting cells from a urine sample, e.g., by centrifugation, and/or directly plating the cells in or on a suitable medium, and/or selecting and isolating urine stem cells based upon stem-specific cell marker expression (e.g., via immunohistochemistry or western blot analysis). Alternatively, urine stem cells may be obtained by collecting and selecting cells via fluorescence-activated cell sorting, e.g., using a marker-specific antibody (e.g., anti-CD117 antibody) conjugated to a fluorophore (e.g., APC, phycoerythrin, allophycocyanins, fluorescein, TEXAS RED, etc.), or magnetic selection using a marker-specific antibody conjugated to magnetic particles. By way of illustration, cells may be incubated with a rabbit polyclonal antibody that specifically binds to the extracellular domain (amino acids 23-322) of the CD117 receptor protein (De Coppi, et al. (2007) Nat. Biotechnol. 25:100). The CD117-positive cells can be purified by incubation with magnetic Goat Anti-Rabbit IgG MicroBeads and selected on a Mini-MACS apparatus. Urine stem cells may also be selected with a monoclonal anti-CD117 antibody directly conjugated to MicroBeads. Any suitable method for selection including attachment to and disattachment from a solid phase is contemplated within the scope of the invention.

Urine stem cells according to some embodiments of the present invention can be routinely passaged or subcultured, e.g., by a 1:4 dilution and permitted to expand to about 50-70% confluency. Isolated populations of urine stem cells can be routinely grown and maintained under conventional culture conditions, e.g., a humidified atmosphere of 5% $CO_2$ at 37° C.

Growth may be accomplished by using initial culture in multiwell plates in a medium supplemented with 5% serum plus epidermal growth factor (EGF).

While cells of the invention can be grown in complex media with KFSM-Stem cell medium (1:1) (Zhang et al., In vitro Cell Dev. Biol.-Animal 37:419, 2001), it will generally be preferable that the cells be maintained in a simple serum-free medium such as KSFM for urothelial stem cells, or medium with 10% FBS for smooth muscle or interstitial stem cells such as Dulbecco's Minimal Essential Media (DMEM), Hank's Basic Salt Solution (HBSS), Dulbecco's phosphate-buffered saline (DPBS), RPMI, or Iscove's-modified Dulbecco's medium (IMDM), in order to effect more precise control over the differentiation of the stem cell into the desired cell.

Serum-free media used according to some embodiments includes endothelium culture medium-2 (EGM-2, Lonza). In other embodiments, a serum free media may be provided that is keratinocyte-serum free medium (KSFM, Sigma) and progenitor cell medium (PCM) in a 1:1 ratio. KSFM can be supplemented with bovine pituitary extract (50 mg/ml), and cholera toxin (30 ng/ml), but in some embodiments does not contain EGF. PCM contains DMEM and Ham's F12 basal media (3:1) supplemented with 0.4 µg/ml hydrocortisone, $10^{-10}$ M cholera toxin, 5 ng/ml insulin, $1.8 \times 10^{-4}$ M adenine, 5 µg/ml transferrin, $2 \times 10^{-9}$ M 3,39,5-triiodo-L-thyronine, and 1% penicillin-streptomycin.

Clone urine stem cell lines can also be generated by a conventional limiting dilution method either in 96-well plates or 24-well plates. Once cell colonies form, the cells are detached and transferred into multi-well dishes.

3. Differentiation of Urine Stem Cells.

Upon appropriate stimulation, USC can be differentiated into various cell types.

"Differentiated" refers to cells or a population containing cells that have specialized functions, e.g., expression of known markers of differentiated cells. In this sense they are not progenitor or stem cells. For example, in some embodiments USC can differentiate into mesenchymal stem cell lineages such as osteocyte, chondrocyte, adipocyte, nerve and muscle cells. Some embodiments of the present invention are subject to the proviso that harvested differentiated cells are not passaged under conditions to create a population of less specialized cells.

In some embodiments, USC are differentiated using methods known in the art for induction of differentiation of multipotent cells into a specific lineage, e.g., osteogenic (bone), chondrogenic (cartilage), adipogenic (fat), neurogenic (nerve), myogenic (muscle), etc. Exemplary of methods of differentiating the USC are provided below.

In some embodiments, USC undergo hypoxia preconditioning by culturing in a 1-2% $O_2$ environment as known in the art (e.g., a humidified incubator at 37° C., at atmospheric pressure, and with 1-2% $O_2$, 5% $CO_2$ and 94% $N_2$) (e.g., for 2, 4, 6, 10, 18, 24, 36 or 48 hours). This may enhance the tissue regenerating ability of USC (see, e.g., Rosova et al., Stem Cells, 2008). It has been demonstrated that mesenchymal stem cells cultured in hypoxic conditions may be able to better differentiate and show enhanced self-renewal (Grayson et al., J. Cell Physiol., 2006; Lennon et al., J. Cell Physiol., 2001).

Osteogenic induction. Seed cells at a density of 4,000 cells/cm$^2$ and culture in DMEM low-glucose medium with 10% FBS (FBS, Gibco/BRL), antibiotics (Pen/Strep, Gibco/BRL), and osteogenic supplements (100 nM dexamethasone, 10 mM beta-glycerophosphate (Sigma-Aldrich), 0.05 mM ascorbic acid-2-phosphate (Wako Chemicals, Irving, Tex.).

Chondrogenic induction. Pellet 3×10$^5$ cells in 0.5 ml of DMEM low glucose medium with antibiotics (Pen/Strep) and chondrogenic supplements (100 nM dexamethasone, 50 µg/ml ascorbic acid phosphate, 5 µg/ml insulin, 5 µg/ml transferrin, 5 ng/ml selenium, 100 µg/ml sodium pyruvate, 40 µg/ml proline, 2 mM L-glutamine, 10 ng/ml TGF-β3) a sterile 15 ml conical polypropylene tube by centrifuging at 600 g for 5 min. Place tubes in the cell culture incubator with the caps loosened to permit gas exchange. The sedimented cells form a spherical mass of cells and float on the media within 24 h. Replace media every three for 21 days.

Adipogenic induction. Seed cells at a density of 10,000 cells/cm$^2$ and culture in DMEM low-glucose medium with 10% FBS, antibiotics (Pen/Strep, Gibco/BRL), and adipogenic supplements (1 mM dexamethasone, 500 mM 3-isobutyl-1-methylxanthine, 10 mg/ml insulin, 100 mM indomethacin (Sigma-Aldrich)) for 21 days with media changes every third day.

Myogenic induction. Seed cells at a density of 3,000 cells/cm$^2$ on plastic plates without coating or coated with Matrigel (Collaborative Biomedical Products; incubation for 1 h at 37° C. at 1 mg/ml in DMEM) in DMEM low-glucose formulation containing 10% horse serum (Gibco/BRL), 0.5% chick embryo extract (Gibco/BRL) and Pen/Strep. Twelve hours after seeding, add 3 mM 5-aza-2'-deoxycytidine (5-azaC; Sigma-Aldrich) to the culture medium for 24 h. Then continue incubation in complete medium lacking 5-azaC, with medium changes every 3 days.

In some embodiments, DMEM low glucose with dexamethasone and hydrocortisone may be used for myogenic induction. In some embodiments, SkGM-2 or SkBM-DM medium with 2% horse serum may be used for myogenic induction.

Endothelial induction. Seed cells at 3,000 cells/cm$^2$ on plastic plates precoated with 0.1% gelatin and maintain in culture for 1 month in endothelial cell medium-2 (EGM™-2, Clonetics; Cambrex Bioproducts) supplemented with 10% FBS, and Pen/Strep. Add Recombinant human bFGF (Stem-Cell Technologies) at intervals of 2 d at 2 ng/ml.

Neurogenic induction. Seed cells at a concentration of 3,000 cells/cm$^2$ on tissue culture plastic plates and culture in DMEM low-glucose medium, Pen/Strep, supplemented with 2% DMSO, 10 mM all-trans retinoic acid (Sigma-Aldrich) and 10 mg/ml basic FGF. After 2 d return the cells to growth medium lacking basic FGF and culture for 10-14 days. Add fresh bFGF every second day.

Other examples of conditions that may be used to differentiate USC according to some embodiments can be found in U.S. Patent Application No. 2005/0124003 to Atala et al. In some embodiments, USC are differentiated using known techniques for differentiating mesenchymal stem cells. See, e.g., U.S. Pat. No. 5,942,225 to Bruder et al., U.S. Patent Publication No. 2006/0057693 to Simon, U.S. Pat. No. 5,811,094 to Caplan et al. See also Pittenger et al., "Stem Cell Culture: Mesenchymal Stem Cells from Bone Marrow," Chapter 38, pp. 461-469, in *Methods of Tissue Engineering* (Atala and Lanza, Eds., 2002).

In some embodiments, growth factors (e.g., nerve growth factor (NGF), aFGF, bFGF, PDGF, TGFβ, VEGF, GDF-5/6/7, BMP-1/2/3/4/5/6/7/13/12/14, IGF-1, etc.) or other mitogenic agents are included in the media or carrier to promote proliferation and differentiation of distinct populations of cells. In this regard, particular embodiments of the invention embrace culturing urine stem cells with selective medium that supports the growth and differentiation of the urine stem cells into urothelial, smooth muscle, interstitial cells, etc.

In some embodiments, USC may be transfected with nucleic acids expressing growth factors or other mitogenic agents. For example, USC according to some embodiments are transfected with the growth factor VEGF (vascular endothelial growth factor). Transfection may be carried out in accordance with methods known in the art.

Differentiation in the present context refers to a status of cells in which the cells develop specific morphological or functional properties. By way of illustration, when urine stem cells are grown in keratinocyte serum-free medium (KSFM) supplemented with 0.09 mM calcium, the cells differentiate into urothelium. Likewise, urine stem cells cultured in DMEM supplemented with serum, e.g., 10% fetal bovine serum (FBS) promotes differentiation into smooth muscle cells.

Determination of whether a USC has differentiated into a specific type of cell can be achieved by morphological analysis and/or the detection of markers specific to these cell types and as generally known in the art. For example, urothelial cells can be identified by the presence of one or more of urothelial-specific markers including, e.g., uroplakin, cytokeratin 7, cytokeratin 13, cytokeratin 17, and cytokeratin 19 and cytokeratin 20; whereas smooth muscle cells can be identified by the presence of one or more smooth muscle-specific markers including, e.g., alpha-smooth muscle actin, desmin, calponin and myosin. Cell type-specific marker expression can be determined using any suitable conventional method include, e.g., immunohistochemistry and/or western blot analyses.

Adipocyte differentiation can be determined by, e.g., the presence of the transcription factor PPARγ and/or lipoprotein lipase (LpL). Chondrocyte differentiation can be determined by, e.g., the presence of chondrogenic lineage markers Sox9, collagen II and/or aggrecan. Osteocyte differentiation can be determined by, e.g., the presence of mineralized bone (von Kossa stain), calcium deposition (Alzarin Red stain), osteocalcin, Runx2 and/or alkaline phosphatase. Endothelial differentiation can be determined by, e.g., the presence of vWF and/or CD 31. Neurogenic differentiation can be determined by, e.g., the presence of nestin.

Moreover, if desired, the cells can be frozen or cryopreserved prior to use, and then thawed to a viable form. Methods of freezing or cryopreserving cells (for subsequent return to viable form) are well known in the art. For example, cryopreservation of cells can involve freezing the cells in a mixture of a growth medium and another liquid that prevents water from forming ice crystals, and then storing the cells at liquid nitrogen temperatures (e.g., from about −80 to about −196° C.). See, e.g., U.S. Pat. No. 6,783,964.

Urothelial cells (UC). In some embodiments, USC can differentiate into cells with urothelial phenotype in KSFM: PCM with 5% FBS and EGF. In other embodiments, serum-free medium is used, e.g., with EGF and low calcium (0.09 mM), to induce urothelium differentiation from USC. If desired, factors can also be used to enhance epithelial differentiation of stem cells, for example, collagen IV (10 µg/ml), bladder extracellular matrix (ECM) (0.1 mg/ml), and/or CM (obtained using primary cultured bladder urothelium, essentially as described below for SMC). Culture dishes in some embodiments are coated with collagen IV or bladder mucosa ECM.

In one embodiment, USC are seeded on tissue culture plastic or matrices, and allowed to grow in KSFM:PCM with EGF for 7 and 14 days, respectively. Culture medium is changed every two days. Cells are analyzed for urothelial differentiation.

The bladder mucosa normally consists of three layers of urothelium (i.e., superficial, interment, and basal urothelium). Uroplakins are urothelium-specific markers, CK20 for superficial urothelium, CK13 for interment, and basal urothelium, and CK7 for all three layers of urothelium. The parameters to evaluate urothelial differentiation of USC include urothelium markers (uroplakin Ia, II, III and CK7, CK13, CK20) and tight junctions assessed with immunohistochemistry, RT-PCR, and western blot.

In some embodiments, UC differentiated from USC show barrier functionality. Permeability barrier function of urothelium can be tested after stratified urothelia consisting of basal, intermediate and superficial cells are induced in physiological concentrations of calcium as described previously (Cross W R, Eardley I, Leese H J, Southgate J. A biomimetic tissue from cultured normal human urothelial cells: analysis of physiological function. Am J Physiol Renal Physiol 2005 August; 289(2):F459-468).

For determination of urea and water permeability of USC and urothelial cultures, diffusive urea and water permeability coefficients can be determined by measuring radioisotopic fluxes. After the TER of the USC and urothelial culture is assessed, 25 µl of [$^3$H] water (200 µCi/ml; Sigma) and 25 1 of [$^{14}$C] urea (200 µCi/ml; Amersham) is added to the apical hemichamber. During the next 60 min, duplicate 100-1 aliquots are taken from both the apical and basal hemichambers at 15-min intervals and placed into 5-ml scintillation vials (PerkinElmer) containing 4 ml Ultima Gold XR scintillation fluid (PerkinElmer). After sampling, the aliquoted volume is replaced with fresh Krebs solution and the TER will be checked to confirm that the USC and urothelial culture have not been physically disturbed. The number of counts of the individual isotopes within the samples will be determined using a Packard Tri-carb 2700TR liquid scintillation counter.

For measurement of dextran permeability of USC and urothelial cultures, permeability assays can be performed using dextran (MW 4,400 and 9,500) conjugated to fluorescein isothiocyanate (FITC). At the start of the experiments, the medium in the apical compartment of the Snapwell membrane is replaced with 500 µl of the appropriate growth medium containing one of the tracers at 1 mg/ml. The basal compartment is replaced with 1 ml of tracer-free growth medium. The induced USC is returned to the incubator for 3 hrs, and then duplicate 350-µl samples will be taken from the basal compartment and the amount of FITC-dextran will be determined using a MFX microtiter plate fluorometer (Dynex). The amount of diffused dextran is calculated from a titration curve of known concentration (3.1-200 mg/ml).

Smooth muscle cells (SMC). In some embodiments, transforming growth factor-beta (TGF-β1, 2.5 ng/ml) plus platelet-derived growth factor (PDGF-BB, 5 ng/ml), or vascular endothelial growth factors (VEGF, 10 ng/ml) are used to differentiate USC into SMC. In some embodiments, USC are cultured in serum-free myogenic differentiation media (MDM) containing DMEM and PCM (1:1) with each of the above combinations of myogenic growth factors. IGF-1 alone or in combination with the above factors may also be used. Cells can be harvested and analyzed for muscle-like characteristics on days 7 and 14 after seeding in induction medium.

An alternative method is to add a low level of serum (1-5%) into the medium 7 days after the cells are cultured in serum-free medium. Cells ($2\times10^3$ cells/cm$^2$) were cultured for 7 days in proliferation medium (DMEM high glucose, 1% FBS, 1% horse serum [HS, GIBCO], 1% CEE [chicken embryo extract, Accurate], 1% PS) and then for 7-10 days in fusion medium (DMEM high glucose, 1% FBS, 1% HS, 0.5% CEE, 1% PS [GIBCO]). Half of the medium is renewed every 4 days. Myogenesis is induced by lowering serum concentration to 2%, and medium is changed every 2 days until elongated myofibers appear.

Differentiation Methods of USC into Different Cell Types

| Target differentiated cell type | Inducing agents | RT-PCR Primers | Western blot Antibodies | Immuno-histochemistry Antibodies | Cell function |
|---|---|---|---|---|---|
| SMC-like cells | 1. VEGF + HFG<br>2. TGF-β1 + PDGF<br>3. CM from bladder SMC | αSMA<br>Desmin<br>Myosin<br>Calponin | αSMA<br>Desmin<br>Myosin<br>Calponin | αSMA<br>Desmin<br>Myosin<br>Calponin | Cell Contractility |

-continued

| Target differentiated cell type | Inducing agents | RT-PCR Primers | Western blot Antibodies | Immuno-histochemistry Antibodies | Cell function |
|---|---|---|---|---|---|
| UC-like cells | 1. EGF<br>2. EGF + VEGF<br>3. CM from urothelium | Uroplakin Ia, II, III<br>P63<br>CK7<br>CK13<br>CK20 | Uroplakin Ia, II, III<br>P63,<br>CK7,<br>CK13, CK20<br>Occludin<br>Zona occludin 1<br>Claudin 1, 2, 4<br>Ion transporter 6H | Uroplakin Ia, II, III<br>P63,<br>CK7, CK13, CK20<br>Occludin<br>Zona occludin 1<br>Claudin 1, 2, 4<br>Ion transporter 6H | Barrier functional assays |

To test cell contractility, differentiation of USC to a SMC fate can be induced by growth for 14 days in serum-free medium with transforming growth factor-β1(TGFβ1, 2.5 ng/ml) plus platelet-derived growth factor (PDGF-BB, 5 ng/ml). Briefly, induced USC, bladder SMC (positive controls), and non-induced USC (negative controls) (each at $3 \times 10^5$ cells/ml) are cultured within a stabilized type I collagen lattices (1 mg/ml). After 5 days of cultivation, the cell-collagen lattice is mechanically released. Contractility action is assayed by measuring the diameter prior to release and at various times after release. A 10-minute time period is used for comparison of the relative amount of contraction for the different lattices. Cell-collagen lattices which will be released in M199 with 10% fetal bovine serum as described above serve as positive controls. For the negative controls, cell-collagen lattices will be washed twice with serum-free media and then further incubated for an additional 5 minutes and released under serum-free conditions. Contractile response to a defined agonist (Ca-ionophore A23187, $10^{-5}$ M) can be performed in a similar manner, except that agonist is added to the serum-free media immediately prior to lattice release.

Smooth muscle tissue produced as described herein may be used in vitro to examine the pharmacological or toxicological properties of compounds of interest (e.g., by adding the compound of interest to a culture medium in which the tissue is immersed, and examining the histological or mechanical properties of the tissue as compared to a control tissue).

Smooth muscle tissue (with or without matrix support) according to some embodiments is "suturable" in that it has sufficient structural integrity to be surgically sutured or otherwise fastened at either end when implanted and thereafter develop tension upon contraction. Smooth muscle tissue produced as described herein may be used for the reconstruction of damaged tissue in a patient, e.g., a patient with a disease traumatic injury of an organ (e.g., bladder).

4. Methods of Treatment.

Urine stem cells and/or cells differentiated from urine stem cells as disclosed herein find use in a variety of methods of treatment.

"Treat" as used herein refers to any type of treatment that imparts a benefit to a patient, e.g., a patient afflicted with or at risk for developing a disease. Treating includes actions taken and actions refrained from being taken for the purpose of improving the condition of the patient (e.g., the relief of one or more symptoms), delay in the onset or progression of the disease, etc.

Diseases that may be treated with the methods disclosed herein include, but are not limited to, augmentation or replacement of urinary tract tissues. For example, urine stem cells may be used in treating diseases and conditions of the urinary tract, e.g., bladder exstrophy; bladder volume insufficiency; reconstruction of bladder following partial or total cystectomy; repair of bladders, kidneys or ureters damaged by trauma; urological cell therapy for patient with stress urinary continence and vesicoureteral reflux, and the like. Treatment in accordance with some embodiment involve urinary tract diseases and conditions such as congenital abnormalities, cancer, trauma, radiation, infection, iatrogenic injuries, nerve injury or other causes. Generally, treatment involves altering urinary tract function; improving urinary tract function; or reconstructing, repairing, augmenting, or replacing damaged urinary tract cells or whole tissues or organs to prevent or treat diseases or conditions of the urinary tract. In this regard, urine stem cells can be used in tissue engineering of urinary tract structures such as ureters, bladders, urethra, renal pelvic, kidney, bone, cartilage, muscle, skin, and the like.

Furthermore, USC find application in the pharmacology of the lower urinary tract and as a non-invasive diagnostic tool for detection of nephrological and/or urinary tract diseases. Cells according to some embodiments of the present invention can be used to diagnose diseases such as hematuria or tumors in the urinary tract system, e.g., tumors of the bladder, renal pelvic, kidney, ureters, prostate gland and urethra; renal diseases such as renal diabetes, renal tubule necrosis, acute or chronic renal failure, and renal rejection after renal transplantation; and other diseases including interstitial cystitis, neuropathic bladder, irradiated bladder, and vesicoureteral reflux or reflux nephropathy. See, e.g., U.S. Pat. Nos. 5,733,739, 5,325,169 and 5,741,648. Examples include, but are not limited to, kidney tumor (clear cell tumor), kidney/ureter transitional cancer, non-invasive bladder cancer (Ta, T1 and CIS), invasive bladder cancer (T2 and above), non-invasive prostate cancer, invasive prostate cancer, diabetes nephropathy, cystitis caused by diabetes, interstitial cystitis, radiational cystitis, renal tubule necrosis, acute renal failure, chronic renal failure, obstruction bladder, urinary incontinence, neuropathic bladder, versicoureteral reflux/reflux nephropathy, ureteropelvic junction obstruction, acute rejection after renal transplantation, chronic rejection after renal transplantation, polycystic kidney disease, kidney stone, etc. Detection may be performed by isolating, culturing and identifying the diseased cells from the collected sample in accordance with techniques known in the art.

Urine stem cells (USC) and cells differentiated from USC find use as a cell source for cell based therapies or tissue engineering. For example, USC may be used in treatment of stress urinary incontinence, in treatment of vesicoureteral reflux, in treatment of muscle dystrophy, in treatment of renal failure, in treatment of cardiac diseases (ischemia heart disease), in treatment of esophageal reflux, in treatment of spinal injury, in treatment of mental diseases such as Parkinson's disease and Alzheimer's disease, as a potential cell source for urinary bladder tissue engineering for patients with bladder cancer and dystrophy (in some embodiments collected from the upper urinary tract to avoid collection of disease cells from the lower urinary tract), for skin substitute in treatment of skin wound or burn injury, plastic surgery in need of a cell source to repair defects, etc. USC from the upper urinary tract may be used for urethral reconstruction with tissue engineering technology.

In some embodiments, USC and/or differentiated USC may be used in the treatment of urinary incontinence. For example, USC and/or USC differentiated into a skeletal myogenic lineage may be used in treatment of urinary stress incontinence in men in which there is urethral sphinctic dysfunction. USC and/or USC differentiated into a smooth muscle cell lineage may be used in treatment of urinary stress incontinence in women in which there is pelvic floor muscle dysfunction.

In some embodiments, USC and/or differentiated USC may be used in the treatment of vesicoureteral reflux, in which there is a smooth muscle tissue defect at the ureteral orifice.

Urine stem cells may also be used in treating diseases and conditions associated with the loss of bone cells, cartilage, etc., in accordance with methods known in the art. See U.S. Pat. No. 5,736,396 to Bruder et al.

In accordance with the present invention, in some embodiments treatment involves administration of an effective amount of urine stem cells, e.g., undifferentiated, differentiated or mixtures thereof, to a subject in need of treatment thereby ameliorating or alleviating at least one sign or symptom of the disease or condition of the subject.

In applications where tissues are implanted, in some embodiments cells are of the same species as the subject into which the tissue is to be implanted. In some embodiments cells are autogeneic (i.e., from the subject to be treated), isogeneic (i.e., a genetically identical but different subject, e.g., from an identical twin), allogeneic (i.e., from a non-genetically identical member of the same species) or xenogeneic (i.e., from a member of a different species).

In some embodiments, when cells of the invention are used for treating a subject, the cells are formulated into a pharmaceutical composition containing the cells in admixture with a pharmaceutically acceptable vehicle or carrier (e.g., a collagen gel). Such formulations can be prepared using techniques well known in the art. See, e.g., U.S. Patent Application 2003/0180289; Remington: *The Science and Practice of Pharmacy*, Alfonso R. Gennaro, editor, 20th ed. Lippincott Williams & Wilkins: Philadelphia, Pa., 2000. In the manufacture of a pharmaceutical formulation according to the invention, the cells are typically admixed with, inter alia, an acceptable carrier. The carrier must, of course, be acceptable in the sense of being compatible with any other ingredients in the formulation and must not be deleterious to the patient. The carrier may be a solid or a liquid, or both (e.g., hydrogels), and can be formulated with the cells as a unit-dose formulation. In one embodiment the cells are provided as a suspension in the carrier to reduce clumping of the cells.

In some embodiments a temperative sensitive gel may be used. Examples of temperature sensitive gels include thermaosensitive hydrogels and thermosensitive polymer gels (e.g., a poloxamer such as Pluronic® F-127 (BASF corporation, Mont Olive, N.J.)). See also U.S. Pat. Nos. 6,201,065, 6,482,435.

In some embodiments, cells are administered in conjunction with other types of cells. For example, in some embodiments USC are administered in conjunction with endothelial cells such as human umbilical vein endothelial cells (HUCEC) in order to promote vascularization. The administration of two or types of cells and/or compounds, etc. "in combination" or "in conjunction" means that the two types of cells and/or compounds are administered closely enough in time to have an additive and/or synergistic effect. They may be administered simultaneously (concurrently) or sequentially. Simultaneous administration may be carried out by mixing prior to administration, or by administering the at the same point in time but at different anatomic sites or using different routes of administration.

In another embodiment, the cells are formulated in an encapsulated form (e.g., encapsulated in a capsule that is permeable to nutrients and oxygen to sustain the viability of the cells in vivo). Materials and methods for the encapsulation of cells in permeable capsules are well known and described in, for example, U.S. Pat. No. 6,783,964. For example, the cells may be encapsulated in a microcapsule of from 50 or 100 nm to 1 or 2 mm in diameter that comprises an internal cell-containing core of polysaccharide gum surrounded by a semipermeable membrane; a microcapsule that comprises alginate in combination with polylysine, polyornithine, and combinations thereof. Other suitable encapsulating materials include, but are not limited to, those described in U.S. Pat. No. 5,702,444.

In a particular embodiment, the cells of the present invention are administered with a biocompatible and/or biodegradable scaffold or matrix. It has been demonstrated that the bladder cells can form normal bladder structures of distinctive layers with urothelium growing on the top of smooth muscle cells after in vitro co-culture on collagen-rich scaffolds (Zhang, et al. (2000) *J. Urol.* 164:928). Additionally, bladder cell-seeded scaffold constructs have been shown to take part in the regenerating process of tissue remodeling in a partial cystostomy model (Zhang, et al. (2005) *BJU Int* 96:1120). Therefore, embodiments of USC find application in engineering cell-scaffold constructs in vitro for later in vivo implantation to completely regenerate the bladder.

A biocompatible scaffold or matrix is any substance not having toxic or injurious effects on biological function, and a biodegradable scaffold is capable of being broken down into its elemental components by a host. Desirably, the scaffold or matrix is porous to allow for cell deposition both on and in the pores of the matrix, and in certain embodiments, is shaped. Such formulations can be prepared by supplying at least one cell population to a biodegradable scaffold to seed the cell population on and/or into the scaffold. In some embodiments the seeded scaffold is then implanted in the body of the recipient subject where the separate, laminarily organized cell populations facilitate the formation of neo-organs or tissue structures.

Biodegradable scaffolds that may be used include, e.g., natural or synthetic polymers, such as collagen (e.g., SIS and BSM), poly(alpha esters) such as poly(lactate acid), poly (glycolic acid), polyorthoesters and polyanhydrides and their copolymers, which can be degraded by hydrolysis at a controlled rate and are reabsorbed. Examples of other suitable materials are provided in U.S. Pat. No. 7,186,554. In some embodiments the scaffold comprises a cellulose polymer, such as a bacterial cellulose polymer. In some embodiments the scaffold comprises hyaluronic acid. In some embodiments the scaffold comprises a polymer selected from PGA/PLGA-PLLA, small intestine submucosa (SIS) and bladder submucose (BSM).

The scaffold can be "shaped" using methods such as, for example, solvent casting, compression molding, filament drawing, meshing, leaching, weaving and coating. In solvent casting, a solution of one or more polymers in an appropriate solvent, such as methylene chloride, is cast as a branching pattern relief structure. After solvent evaporation, a thin film is obtained. In compression molding, a polymer is pressed at pressures up to 30,000 pounds per square inch into an appropriate pattern. Filament drawing involves drawing from the molten polymer and meshing involves forming a mesh by compressing fibers into a felt-like material. In leaching, a solution containing two materials is spread into a shape that resembles the final form. Next, a solvent is used to dissolve away one of the components, resulting in pore formation (see U.S. Pat. No. 5,514,378). In nucleation, thin films in the shape of a reconstructive urothelial graft are exposed to radioactive fission products that create tracks of radiation damaged material. Next the polycarbonate sheets are etched with acid or base, turning the tracks of radiation-damaged material into pores. Finally, a laser may be used to shape and burn individual holes through many materials to form a reconstructive urothelial graft structure with uniform pore sizes. These shaping techniques may be employed in combination. For example, a biodegradable matrix can be weaved, compression molded and also glued. Furthermore, different polymeric materials shaped by different processes may be joined together to form a composite shape. The composite shape can be a laminar structure. For example, a polymeric matrix can be attached to one or more polymeric matrixes to form a multilayer polymeric matrix structure. The attachment can be performed by gluing with a liquid polymer or by suturing. In addition, the polymeric matrix can be formed as a solid block and shaped by laser or other standard machining techniques to its desired final form. Laser shaping refers to the process of removing materials using a laser.

The scaffold can be treated with additives or drugs prior to implantation (before or after it is seeded with cells), e.g., to promote the formation of new tissue after implantation. Thus, for example, growth factors, cytokines, extracellular matrix components, and/or other bioactive materials can be added to the biodegradable scaffold to promote graft healing and the formation of new tissue. Such additives will, in general, be selected according to the tissue or organ being reconstructed or augmented, to ensure that appropriate new tissue is formed in the engrafted organ ox tissue. For examples of such additives for use in promoting bone healing, see, e.g., Kirker-Head (1995) Vet. Surg. 24 (5):408-19.

Seeding of cells onto the scaffold may be performed according to standard methods. For example, the seeding of cells onto polymeric substrates for use in tissue repair has been reported (see, e.g., U.S. Pat. No. 6,171,344 to Atala, which is incorporated by reference herein; Atala et al. (1992) J. Urol. 148:658-62; Atala et al. (1993) J. Urol. 150:608-12). As an example, cells grown in culture can be trypsinized to separate the cells, and the separated cells can be seeded on the biodegradable scaffold. Alternatively, cells obtained from cell culture can be lifted from a culture plate as a cell layer, and the cell layer can be directly seeded onto the biodegradable scaffold without prior separation of the cells.

The density of cells seeded onto the scaffold can be varied. For example, in some embodiments greater cell densities promote greater tissue formation by the seeded cells, while lesser densities can permit relatively greater formation of tissue by cells infiltrating the graft from the host. Other seeding techniques can also be used depending on the biodegradable scaffold and the cells. For example, the cells can be applied to the biodegradable scaffold by vacuum filtration. Selection of cell types and seeding cells onto a biodegradable scaffold will be routine to one of ordinary skill in the art in light of the teachings herein.

In further embodiments, formulations of the invention include those for parenteral administration (e.g., subcutaneous, intramuscular, intradermal, intravenous, intraarterial, intraperitoneal injection) or implantation. In some embodiments, administration is carried out intravascularly, either by simple injection, or by injection through a catheter positioned in a suitable blood vessel, such as a renal artery. In another embodiment, administration is carried out as a graft to an organ or tissue to be augmented, as discussed above.

Formulations of the present invention suitable for parenteral administration include sterile liquid, preferably aqueous, injection compositions of the cells, which preparations may be isotonic with the blood of the intended recipient. These preparations can also contain anti-oxidants, buffers, bacteriostats and solutes that render the formulation isotonic with the blood of the intended recipient. The preparations are, apart from the cells being administered, sterile in the sense that they are free of microbial contaminants such as bacteria and viruses. The formulations can be in a synringeable, injectable form, can be in a form suitable for surgical implantation, or in any other form suitable for administration into the subject.

According to some embodiments, the cells administered to the subject can be syngeneic (i.e., isologous, including isogeneic and autogeneic), allogeneic (i.e., homologous) or xenogeneic (i.e., heterologous) with respect to the subject being treated, depending upon other steps such as the presence or absence of encapsulation or the administration of immune suppression therapy of the cells.

The therapeutically effective dosage of cells will vary somewhat from subject to subject, and will depend upon factors such as the age, weight, and condition of the subject and the route of delivery. Such dosages can be determined in accordance with procedures known to those skilled in the art. In general, in some embodiments, a dosage of $1 \times 10^5$, $1 \times 10^6$ or $5 \times 10^6$ up to $1 \times 10^7$, $1 \times 10^8$ or $1 \times 10^9$ cells or more per subject may be given, administered together at a single time or given as several subdivided administrations. In other embodiments a dosage of between $1$-$100 \times 10^8$ cells per kilogram subject body weight can be given, administered together at a single time or given as several subdivided administrations. Of course, follow-up administrations may be given if necessary.

For allogenic transplant into a patient, cells and/or tissues as described herein may be matched or tissue-typed in accordance with known techniques, and/or the subject may be administered immune suppressive agents to combat tissue transplant rejection, also in accordance with known techniques. If desired or necessary, the subject can also be administered an agent for inhibiting transplant rejection of the administered cells, such as rapamycin, azathioprine, corticosteroids, cyclosporin and/or FK506, in accordance with known techniques. See, e.g., U.S. Pat. Nos. 5,461,058; 5,403,833; and 5,100,899; see also U.S. Pat. Nos. 6,455,518; 6,346,243; and 5,321,043.

Moreover, cells of the present invention can be transfected (e.g., with a specific gene) prior to seeding with genetic material. Useful genetic material may be, for example, genetic sequences that are capable of reducing or eliminating an immune response in the host. For example, the expression of cell surface antigens such as class I and class II histocompatibility antigens can be suppressed. This would allow the transplanted cells to have a reduced chance of rejection by the host.

Kits for Collecting USC.

Kits are also provided herein for the collection of urine samples. Preferably kits according to the present invention serve to preserve the viability of urine stem cells during transport to a remote location (e.g., a suitable laboratory facility). In some embodiments, kits include a tube containing a suitable media (e.g., 1-15 mL, and in some embodiments 5 mL of a serum such as fetal bovine serum). The media may be provided frozen, to be thawed before use. In other embodiments, kits include a tube containing antibiotics (e.g., 1-15 mL, and in some embodiments 5 mL of a solution containing 1% penicillin and streptomycin). The antibiotics may be in powder form or in aqueous solution (optionally provided frozen, to be thawed before use).

Kits may also include suitable containers (e.g., bottles) for the collection of urine samples (e.g., three sterile plastic bottles of a suitable volume, e.g., 100-1,000 mL, and in some embodiments 500 mL). Kits may also include alcohol swabs. In some embodiments cooling means such as ice bags, cold packs, etc., are included to keep urine cool at approximately 4° C. (e.g., 2 ice bags having dimensions of 3 inch×2 inc×0.5 inch). Further embodiments include a container that can hold the above listed components (e.g., a plastic box having dimensions of 6 inch tall×6 inch wide×7 inch long), and optionally also includes instructions for use.

The present invention is explained in greater detail in the following non-limiting examples.

EXAMPLE 1

Isolation and Characterization of Stem Cells from Urine

Fifty-eight human urine samples were collected from 22 male and one female donors (15 healthy individuals and 8 patients), ranging in age from 2 to 50 years. No bacterial contamination was found in any cultures. Urine samples were centrifuged at 1500 RPM for 5 minutes at 4° C. and washed two times with sterile PBS. Cells were plated at an average of 0.5 cell/well in multi-well plates with stem cell medium using a gradual dilution method. The stem cell medium contains ¾ DMEM, ¼ Ham's F12, 10% FBS, 0.4 mg/ml hydrocortisone, $10^{-10}$ M, Chron Toxin, 5 mg/ml, insulin, 1.2 mg/ml adenine, 2.5 mg/ml transferrin plus 0.136 mg/ml 3,39,5-triiodo-L-thyronine, 10 mg/ml EGF, and 1% penicillin-streptomycin (Zhang et al., In vitro Cell Dev. Biol.-Animal 37:419, 2001). Single cells were identified and allowed to grow to more than 50% confluence. Cells were subsequently subcultured, transferred to a 6-cm culture dish and expanded.

Primary cell outgrowth was obtained in about 39% of the cultures initiated from urine samples. Average numbers of cells in the colony were 4.5/100 ml urine in healthy individuals on the second day (Table 1). The cells were small, brighter-looking cells that were most likely from the base layer of the bladder mucosa, and relatively undifferentiated based upon our experience with long-term observation (FIG. 1). A consistently high yield of urine cells was achieved from each clonal line. Cell doubling time of urine cells was 31.3 hours in a complex media with stem cell medium and KSFM (1:1). It took 10 to 12 days for urine cells from a single cell to reach confluence in a 6-cm culture dish (FIG. 2).

TABLE 1

| | | Number of Urine Samples | Average of Clone #/100 ml Urine | Percentage of Colony Formation |
|---|---|---|---|---|
| Age | | | | |
| 2 yrs or younger | | 6 | 3.3 | 37% (7/17) |
| 13-40 yrs old | | 6 | 5.8 | 50% (8/16) |
| >40 yrs old | | 6 | 3.5 | 38% (7/16) |
| Sources | | | | |
| Morning Urine | | 6 | 4.5 | 50% (6/12) |
| Fresh Urine | | 6 | 7.2 | 65% (11/17) |
| Storage at 4° C. | 4 hours | 6 | 2.3 | 38% (3/8) |
| | 8 hours | 6 | 1.2 | 17% (1/6) |
| | 24 hours | 6 | 0.2 | 17% (1/6) |

To demonstrate molecular and cellular features of the urine cells, expression of stem cell-specific and differentiated cell-specific markers was analyzed. Urine cells at passage 1, 3 and 4 all stained positively for stem cell-specific surface markers, including C-kit$^+$, SSEA-4$^+$, CD105$^+$, CD73$^+$, CD90$^+$, CD133$^+$, and CD44$^+$ and stained negatively for CD31$^-$, CD34$^-$, and CD45$^-$ (Table 2 and FIG. 3). CD44 is considered a cell surface marker for bladder base cells (Desai, et al. (2000) *Mod. Pathol.* 13:1315). Since base cells have the potential to self-renew and can proliferate and differentiate into intermediate and superficial cells, base cells are referred to as urothelial stem cells or stem cells (Staack, et al. (2005) *Differentiation* 73:121). Basal cells in the urine were confirmed by CD44 and immunofluorescence with cytokeratin 13, an intracellular protein marker for the basal and intermediate cell (Romih, et al. (2005) *Cell Tissue Res.* 320:259).

TABLE 2

| CD Antigens | Passage 1 (%) | Passage 3 (%) | Passage 4 (%) |
|---|---|---|---|
| C-kit (CD117) | 7 | 2 | 0.5 |
| SSEA-4 | — | 72 | 75 |
| CD105 | 93 | 86 | 71 |
| CD73 | — | 62 | 41 |
| CD90 | 90 | 83 | 89 |
| CD133 | — | 2 | 10 |
| CD44 | 95 | 67 | 40 |
| CD31 | — | 0.5 | 0 |
| CD34 | 0 | 0 | 0 |
| CD45 | — | 1 | 0.5 |

It seems that there are mixed cell populations in urine: stem cells and mature cells as well. Urine was found to contain urothelial stem cells and smooth muscle stem cells. These cells were confirmed with CD markers as indicated above. In addition, urothelial stem cell markers and smooth muscle cell markers were employed to further characterize these cells. Monoclonal antibodies against urothelial stem cell-specific markers, uroplakin Ia and cytokeratins 7, 13, 17, and 19, were applied at 70% cell confluence, at the following dilutions for each antibody: anti-cytokeratin 7, 1:200; anti-cytokeratin 13, 1:100; anti-cytokeratin 17, 1:100; and anti-cytokeratin 19, 1:100. The expression of uroplakin and the indicated cytokeratins in urine stem cells was determined and compared with the expression of the markers in cultured urothelium obtained from regular biopsy tissue (Zhang, et al. (2003) *Adv. Exp. Med. Biol.* 539:907;

Ludwikowski, et al. (1999) *BJU Int.* 84:507; Sugasi, et al. (2000) *J. Urol.* 164:951; Zhang, et al. (2001) *In Vitro Cell Dev. Biol, Anim.* 37:419) as well as normal human bladder mucosa (Southgate et al., *Lab Investigation* (1994) 71:583). The degree of immunofluorescence was defined as ranging from negative (−) to strongly positive (++++). Similar to cultured urothelium obtained from tissue biopsy, urine cells expressed uroplakin Ia and cytokeratins (CK) 7, 13, 17, and 19 (FIG. 4A-FIG. 4H and Table 3).

TABLE 3

| Specificity | Normal Human Bladder Mucosa | | | Cultured Urothelium from Biopsy | Cultured Urine Cells |
| --- | --- | --- | --- | --- | --- |
| | Basal Cells | Intermediate Cells | Superficial Cells | | |
| CK7 | ++ | ++ | ++ | +++ | ++ |
| CK13 | ++ | ++ | − | + | + |
| CK17 | ++ | ++/− | ++/− | ++ | ++ |
| CK19 | ++ | ++/− | ++ | ++ | ++ |
| Uroplakin 1a | − | − | +++ | ++ | ++ |

Moreover, compared to native bladder cells, cells obtained from urine expressed smooth muscle cell-specific markers, alpha smooth muscle actin (ASMA), desmin, myosin and calponin, as determined by immunofluorescence (FIG. 5 and Table 4).

TABLE 4

| Specificity | Normal Human Bladder Tissue | | | Cultured Urothelium from Biopsy | Cultured Urine Cells |
| --- | --- | --- | --- | --- | --- |
| | SMC | Myo-fibroblast | Interstitial Cells | | |
| ASMA | ++++ | +++ | +++ | ++++ | +++ |
| Desmin | ++ | − | − | + | + |
| Myosin | ++ | − | − | + | + |
| Calponin | +++ | − | − | +++ | +++ |
| C-Kit | | | | + | + |

EXAMPLE 2

Cell Contractility and Tight Junctions of Urine Stem Cells

Functional characteristics of urine-derived smooth muscle cells are ascertained by determining cell contractility with collagen lattices. Methods for the collagen lattice contraction assay are known in the art (Kropp, et al. (1999) *J. Urol.* 162:1779). Contractile response to agonists is performed in a similar manner except that agonists are added to the serum-free media immediately prior to lattice release. Agonists which are tested include the Ca-ionophore A23187 (1025 M) and KCl.

Urine-derived urothelial stem cells are analyzed for tight junctions. Urothelial barrier function is maintained by apical membrane plaques and intercellular tight junctions. Tight junction components within urine stem cells is investigated with conventional methods such as electric microscopy (Zhang, et al. (2003) *Adv. Exp. Med. Biol.* 539:907; Ludwikowski, et al. (1999) *BJU Int* 84:507; Sugasi, et al. (2000) *J. Urol.* 164:951; Zhang, et al. (2001) *In Vitro Cell Dev. Biol. Anim.* 37:419; Cross, et al. (2005) *Am. J. Physiol. Renal Physiol.* 289:F459).

EXAMPLE 3

Urine Stem Cell Differentiation into Smooth Muscle Cells

To determine the effect of epithelial-stromal cell interaction or cell-cell interaction on urine stem cell differentiation into smooth muscle cells (Staack, et al. (2005) *Differentiation* 73:121; DiSandro, et al. (1998) *J. Urol.* 160:1040), two co-culture methods are used. The first is an indirect co-culture using transwell devices with a 4.5 μm size exclusion. Urine smooth muscle stem cells are plated on the upper chamber wells and bladder smooth muscle cells and/or urothelium from tissue biopsy are seeded on the bottom wells of a transwell unit (Luk, et al. (2005) *J. Immunol. Methods* 305:39; Gerstenfeld, et al. (2003) *Connect Tissue Res.* 44(suppl 1):85). The second method is a direct co-culture approach which is performed with a transwell insert of 0.4 μm pore size. The transwell is used as a basement membrane on which urine stem cells are cultured on the lower side, while normal human bladder urothelium and smooth muscle cells are cultured on the opposite upper side (Le Visage, et al. 92004) *Tissue Eng.* 10:1426). The urine cells are subsequently evaluated through phenotypic appearance, molecular analysis and immunohistochemical staining for smooth muscle protein expression on days 3, 7, 14, and 28 after cell seeding.

EXAMPLE 4

Scaffolds Seeded with Urine Stem Cells

Cell attachment, proliferation and differentiation of urine stem cells on bladder submucosa membrane (BSM) and small intestine submucosa (SIS) was evaluated to determine the cell-matrix interaction for clinical application. In in vitro cell-seeded constructs, urine stem cell-derived urothelium was seeded on the BSM mucosal side and urine stem cell-derived smooth muscle cells on the serosa side placed in the presence of mixed media (KSFM:DMEM, 1:1).

Subsequently, the seeded matrices were implanted subcutaneously into athymic mice. The implanted engineered tissues were retrieved and assessed via histochemistry (H&E and Trichrom), immunohistochemistry (cytokeratin and smooth muscle cell-specific markers), western blot analyses, and human X/Y chromosome detection assay (FISH). For histochemical and immunohistochemical analysis, engineered tissues were fixed in 10% neutral-buffered formalin, dehydrated, and embedded in paraffin, using standard procedures. Five-mm sections were cut and mounted. Routine hematoxylin and eosin (H&E) staining and Masson's trichrome staining were performed. Immunohistochemical staining was also performed using monoclonal antibodies against smooth muscle cell proteins, alpha-smooth muscle actin (diluted 1:1000), desmin (1:20), calponin (1:50) and myosin (1:100) and against urothelial cell-specific protein, cytokeratin AE 1/AE3 (1:100 antibody dilution) (Zhang, et al. (2005) *BJU Int.* 96:1120; Zhang, et al. (2003) *Adv. Exp. Med. Biol.* 539:907; Zhang, et al. (2000) *J. Urol.* 164:928; Zhang, et al. (2006) *BJU Int.* 98:1100; Zhang, et al. (2004) *Tissue Eng.* 10:181; Zhang, et al. (2001) *In Vitro Cell Dev. Biol. Anim.* 37:419).

Proteins for western blot analysis were isolated by lysing cells or the cell-seeded scaffold tissue with a lysis buffer according to known methods (Zhang, et al. (2005) *BJU Int.* 96:1120; Lin, et al. (2004) *J. Urol.* 171:1348). Mouse anti-human alpha-smooth muscle actin, desmin, myosin, and AE1/AE3 were used as the primary antibody and peroxidase-labeled goat anti-mouse IgG as the secondary antibody. The presence of protein bands was detected by a commercially available enhanced chemiluminescence assay kit.

Urine stem cells were noted in the graft tissues with LacZ staining one month after implantation. The implanted cells were also confirmed by human X/Y chromosome. Advantageously, urine stem cells formed multilayered urothelial cells and smooth muscle-like tissue structures within the scaffolds in vivo (FIG. 6A-FIG. 6D). Furthermore, no tumor was observed in the graft tissues three months after implantation.

These data therefore provide in vitro and in vivo evidence that cells obtained from urine can serve as a source for tissue engineering and cell therapy applications. Urine stem cells are readily available, and it has been shown that they proliferate and differentiate into urothelium and smooth muscle in vitro. Bladder cells derived from urine stem cells show urothelium and smooth muscle-like phenotypes including expressing urothelium and smooth muscle-specific proteins, respectively. Collagen matrix supports the three-dimensional growth of urine stem cells, which is a basic requirement for bladder reconstruction. In vivo urine stem cells-seeded scaffolds provide a cost-effective method for bladder reconstruction.

EXAMPLE 5

Osteogenic Differentiation of Human Urine Stem Cells

Figure 7:
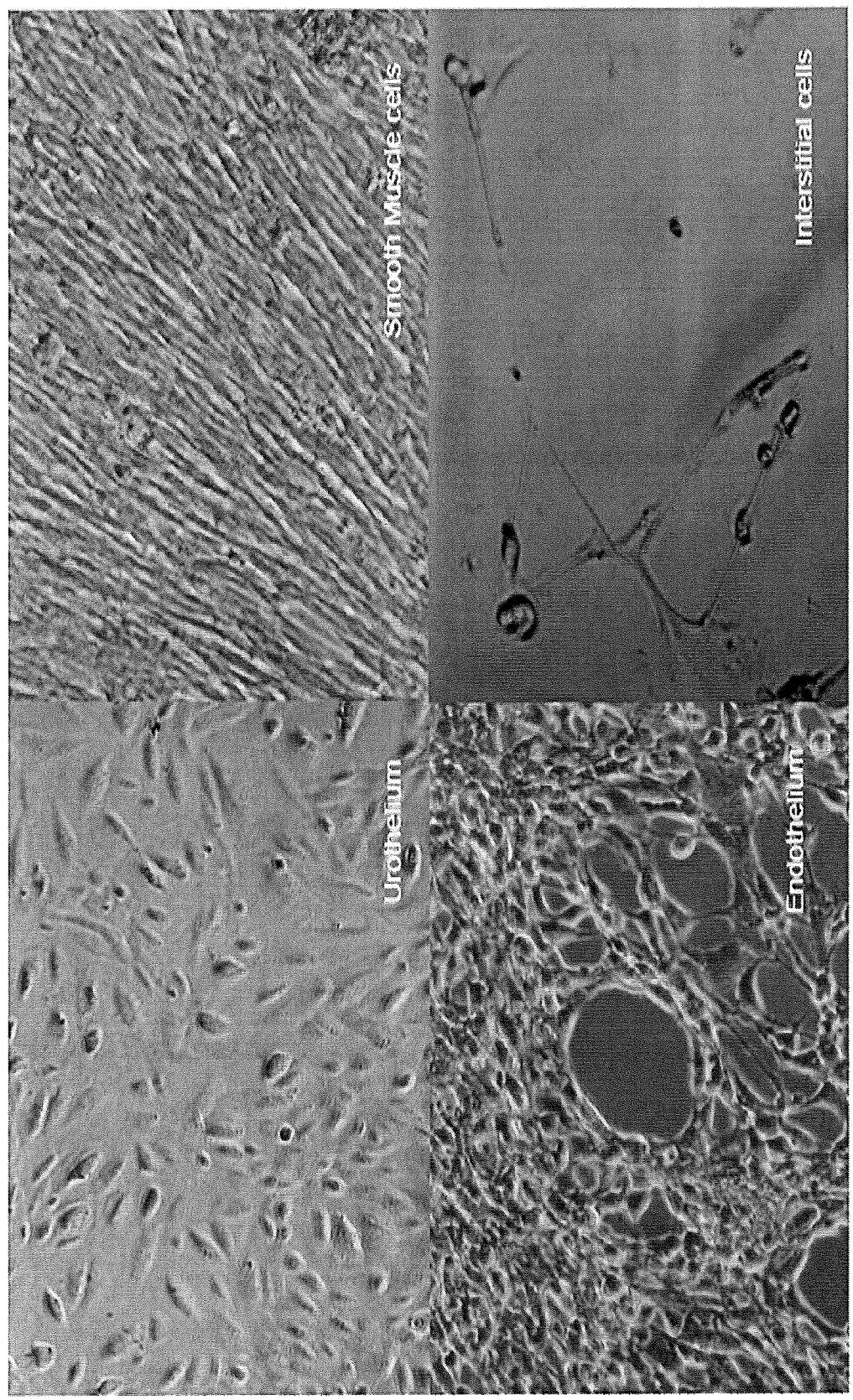
FIG. 7. Four cells types observed in cultured urine cells: endothelial-like, smooth muscle-like, epithelial-like and interstitial-like cells.
Figure 8:
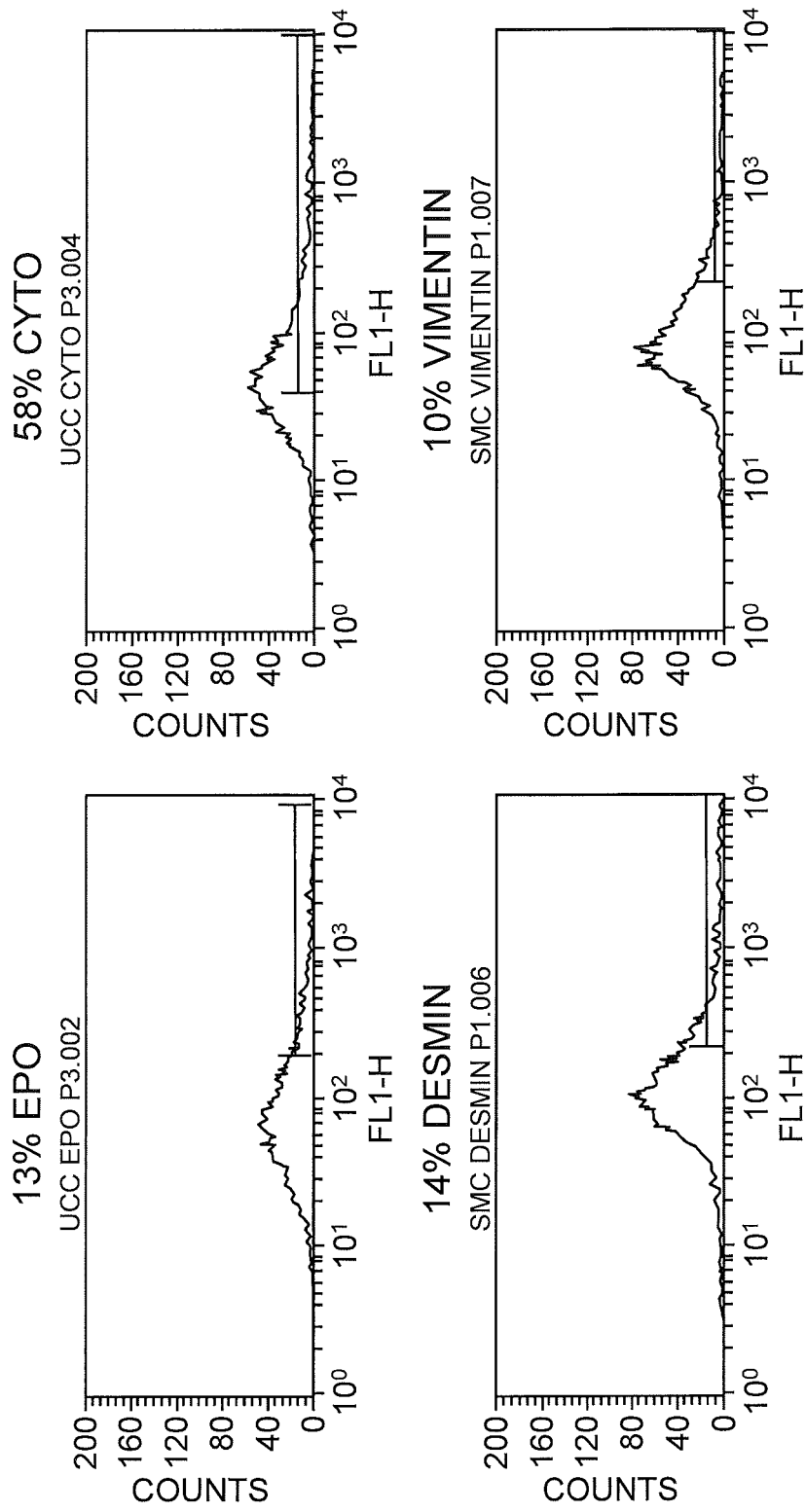
FIG. 8. Cells were analyzed by FACS for cell-specific markers AE1/AE3, Desmin, Vimentin and Erythropoietin.

Traditional approaches for treatment of bone defects caused by injury or disease rely on the presence of osteo-stem cells at the site of injury. In cases where these osteo-stem cells are compromised, other cell sources are required for cell-based therapy. We have identified such a cell source in human urine. The studies described in the examples above demonstrated that urine stem cells (USC) possess the potential to differentiate into bladder cell lineages (FIG. 7) and these cells may be able to differentiate into other cell types, including bone cells. Successful generation of bone cells from urine would circumvent other expensive methods of sourcing autologous cells and would be a simple, cost effective and safe method for collecting cells for bone therapy.

Thirty-one urine samples were collected from six healthy individuals and USC were isolated and expanded from these samples as described in the examples above. USC were plated on laminin coated dishes and cultured in KSFM/EFM (1:1) media until 80% confluency was achieved. USC at passage 3 were used for cell differentiation. To induce osteogenic differentiation, osteogenic media (DMEM containing dexamethasone, β-glycerophosphate and ascorbic acid) was added and media was changed every 2-3 days. The treated USC were assayed for expression of bone markers (osteocalcin, alkaline phosphatase and β-microglobulin) by RT-PCR and immunohistochemical staining on day 28. Non-induced USC were used as negative control and human bone marrow derived mesenchymal stem cells as positive control.

Immunohistochemical staining using Alizarin Red S dye showed that USC produced calcium 28 days after treatment with osteogenic media, as seen by the intense red foci on the top right panel of FIG. 11. The control did not stain for calcium. In addition, treated USC expressed alkaline phosphatase (ALP-2), which bone cells require for calcium deposition. Intense purple staining of the induced cells was seen (FIG. 11). RT-PCR performed on USC induced with osteogenic media for 28 days showed expression of highly specific bone-related transcripts only with the osteogenic treatment. Control USC cells and -RT control showed no amplification of these transcripts (FIG. 12).

UPCs can be induced to differentiate into bone-like cells by using media containing osteogenic supplements. The induced cells secrete calcium and synthesize alkaline phosphatase as seen in normal bone cells. We conclude that USC may be used for bone regeneration.

EXAMPLE 6

Urine Stem Cells Show Multipotency

Historically, efforts to isolate cells from urine, presumably originating in the bladder and perhaps the kidney and ureters, met with poor success. However, we herein describe conditions under which urine stem cells can be expanded from essentially any individual. As shown in the Examples above, we have successfully isolated stem cells from human urine (see also PCT Application No. PCT/US2008/006438, published as WO 2008/153685, which is incorporated by reference herein). We demonstrated a reproducible harvest, isolation and in vitro expansion of USC and differentiation of USC into bladder smooth muscle cells (SMC) and urothelium in culture, as well as osteogenic differentiation.

Below, we demonstrate differentiation of USC into multiple cell lineages characteristic of MSCs. We have, therefore, termed the cells urine stem cells (USC) due to their mesenchymal stem cell-like phenotype and ability to differentiate into multiple cell lineages. (This is a change from the urine progenitor cells (UPC) terminology used in PCT Application No. PCT/US2008/006438.)

We observed that the major population of cells collected from urine are terminally differentiated urothelium and do not attach well to tissue culture plastic. Some other cells attach but show limited growth. However, we consistently found that small numbers of cells were able to grow as colonies that continued to expand and could be passaged multiple times. By initially plating samples in multi-well dishes (24 or 96 wells), we found that individual urine-derived cells can be grown immediately as cell clones. The cells capable of such clonal growth are those we term urine-derived stem cells (USC).

The USC are small, compact, diploid cells. They typically show a doubling time of 31.3 hours in the stem cell medium we developed and described in Example 1 above. In 10-12 days, a single cell can be expanded to reach confluence in a 3.5-cm culture dish. The cells can then be subcultured multiple times. In general, we have found that individual clones can be expanded to $10^6$-$10^7$ cells (or about 20-25 population doublings [pd] from an initial cell harvested from urine) while maintaining marker expression and their ability to differentiate. Although we can finally obtain as many as $1 \times 10^9$ cells from a clone (about 30 pd), growth slows and the cells spread and become flattened, and no longer differentiate well. These growth parameters are roughly comparable to those typically described in the literature for MSCs.

We reported that fresh urine obtained from urination yielded 4.5-7.2 USC clones per 100 ml urine, depending on time of day. The yield from urine obtained by catheterization was at least 4-fold greater. Storage of urine for more than 4 hours was deleterious to the recovery of viable colony-forming cells. We noted a possible trend for urine of younger subjects (under age 13) to give a slightly lower yield of USC than for older subjects. However, this did not reach statistical significance. Overall, we obtained clones from about 40-50% of samples.

We now obtain USC clones from more than 90% of urine samples by the following modifications of the collection procedure: 1) After mid and last stream urine was collected, urine sample is centrifuged and cell pellets washed with phosphate-buffered saline (PBS) containing 5% FBS. 2) If urine is clear, urine sample is centrifuged and then cells are plated on culture dishes directly. We found that PBS wash decreases the rate of cell colony formation and survival. The best way is to avoid to wash cells with pure PBS. If urine has to be washed, culture medium or PBS with 5% serum is recommended. In the rare cases where clones are not obtained, collection of a repeat sample from the same individual usually succeeds.

A. Stem Cell Surface Makers on USC

We used monoclonal antibodies and flow cytometry (FACS) to assess markers expressed by human USC (Table 1, supra Example 1). Three independent clones gave similar results. A high percentage of cells initially expressed markers shared with MSCs, including CD44 (also a marker for basal cells of the bladder mucosa), CD73, CD90, and CD105. Expression of most of these markers was maintained as cells were expanded to passage 4. Hematopoietic and endothelial lineage markers (CD31, CD34, CD45) were not expressed. SSEA4 was expressed by about 75% of cells. This glycolipid antigen is a marker of human ES cells, and also of long-lived, broadly multipotent stem cells from human amniotic fluid previously described (see De Coppi et al. (2007) Nature Biotechnology 25(1):100-6; PCT Application WO 03/042405 to Atala and DeCoppi). However, SSEA4 also is expressed by MSCs under certain culture conditions. Markers associated with other stem cells, namely CD117 and CD133, were detected on small percentages of cells.

B. Urothelial Differentiation of USC

Figure 3:
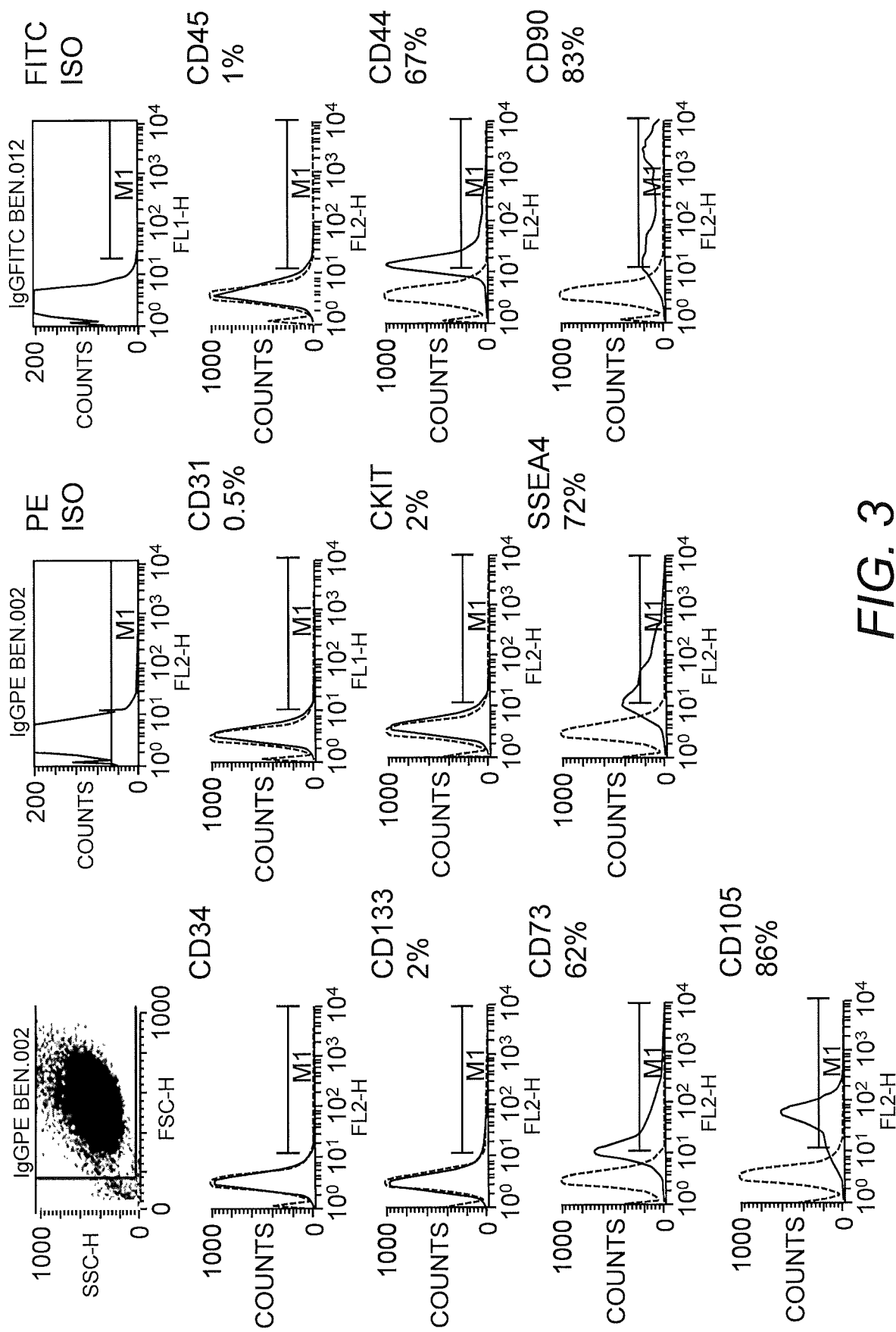
FIG. 3. Graphs of fluorescence activated cell sorting (FACS) demonstrate the presence of stem cell markers such as CD44, 105, 73, 90 and 133 in cells isolated from urine.
Figure 6B:
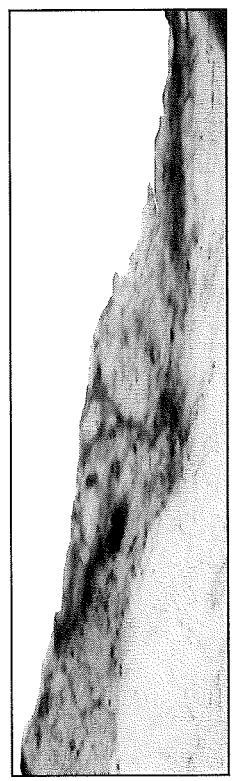
FIG. 6A-FIG. 6D. Histological features of USC-bladder submucosa membrane (BSM) and USC-small intestine submucosa (SIS) constructs one month after implantation in vivo.
Figure 6D:
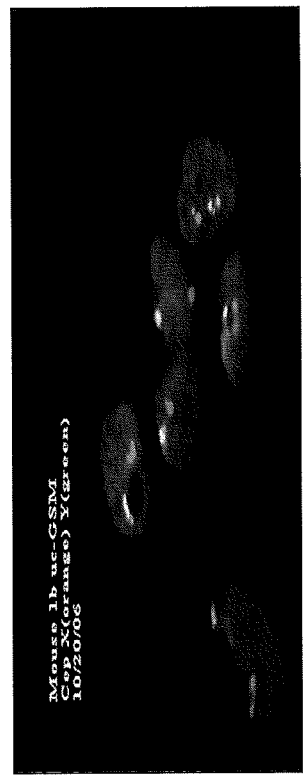
Figure 6A:
Figure 6C:
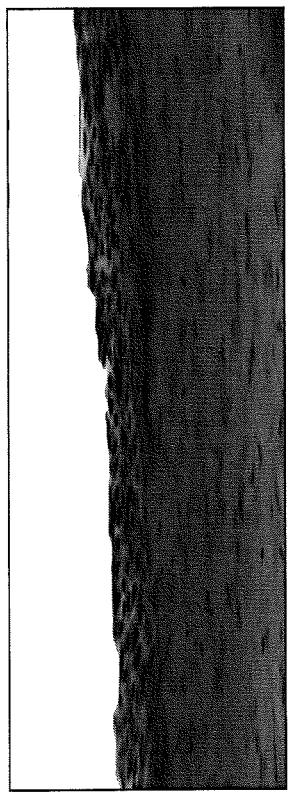

When USC were cultured in keratinocyte serum-free medium (KSFM) containing epidermal growth factor (EGF) and low calcium (0.09 mM), the cells were induced to express proteins characteristic of differentiated urothelium. These included cytokeratins (CK7, CK13, CK19) and uroplakin Ia, assessed by immunofluorescence, western immunoblotting, and FACS analysis (FIG. 3).

C. Smooth Muscle Cell Differentiation of USC

USC also were capable of being induced to express markers consistent with the smooth muscle cell (SMC) lineage. Culturing in DMEM with 10% fetal bovine serum (FBS) and myogenic growth factors (TGF-β1+PDGF-BB) induced a change in morphology from cobblestone to an elongated spindle shape. Decellularized bladder matrix somewhat enhanced the change, but only in the presence of the myogenic factors. We found that non-induced USC also express detectable levels of several SMC markers (especially α-smooth muscle actin [αSMA] and calponin, along with low levels of desmin and myosin), as judged by immunocytochemistry, RT-PCR, western blotting and immunofluorescence. Expression of the muscle markers increased markedly over 1-2 weeks of exposure to myogenic medium. However, desmin and αSMA levels did not reach those seen with authentic bladder SMC from tissue biopsies. Note that expression of low levels of αSMA and desmin also is characteristic of uninduced MSCs and pericytes.

D. Multipotency of Cloned USC

The similarities in surface marker phenotype and gene expression led us to ask whether USC can differentiate to lineages typical for MSCs. We tested USC cell clones obtained from 11 independent donors. USC could be induced to express markers typical of the osteogenic, adipogenic, and chondrogenic lineages, using differentiation protocols that have been employed routinely with MSCs, and were used previously by members of our Institute associated with this application to assess the differentiation capacity of amniotic fluid-derived stem cells (see De Coppi et al. (2007) Nature Biotechnology 25(1):100-6; PCT Application WO 03/042405 to Atala and DeCoppi, incorporated by reference herein). The results of immunohistochemical staining (FIG. 13A-FIG. 13F) and transcript analysis by RT-PCR (FIG. 13G-FIG. 13I) were consistent.

Differentiation of USC to adipocyte-like cells. Adipogenic induction. Cells were seeded at a density of 10,000 cells/cm$^2$ and culture in DMEM low-glucose medium with 10% FBS, antibiotics (Pen/Strep, Gibco/BRL), and adipogenic supplements (1 mM dexamethasone, 500 mM 3-isobutyl-1-methylxanthine, 10 mg/ml insulin, 100 mM indomethacin (Sigma-Aldrich)) for 21 days with media changes every third day. Adipogenic differentiation was assessed by Oil Red O staining (FIG. 13A) and RT-PCR for the transcription factor PPARγ and lipoprotein lipase (LpL) (FIG. 13G).

Differentiation of USC to cartilage-like cells. Chondrogenic induction. Pellet 3×10$^5$ cells in 0.5 ml of DMEM low glucose medium with antibiotics (Pen/Strep) and chondrogenic supplements (100 nM dexamethasone, 50 µg/ml ascorbic acid phosphate, 5 µg/ml insulin, 5 µg/ml transferrin, 5 ng/ml selenium, 100 µg/ml sodium pyruvate, 40 µg/ml proline, 2 mM L-glutamine, 10 ng/ml TGF-β3) a sterile 15 ml conical polypropylene tube by centrifuging at 600 g for 5 min. Tubes were placed in the cell culture incubator with the caps loosened to permit gas exchange. The sedimented cells formed a spherical mass of cells and floated on the media within 24 h. Media was replaced every three for 21 days. Alcian Blue and Toluidine Blue staining of glycosaminoglycans (GAGs) indicated chondrogenic differentiation of USC induced with TGF-β3 (FIG. 13B, FIG. 13C). RT-PCR of control USC (lane 1) and USC induced with TGF-β3 (lane 2) confirmed induction of chondrogenic lineage markers Sox9, collagen II and aggrecan (FIG. 13H).

Differentiation of USC to osteocyte-like cells. Osteogenic induction. Cells were seeded at a density of 4,000 cells/cm$^2$ and culture in DMEM low-glucose medium with 10% FBS (FBS, Gibco/BRL), antibiotics (Pen/Strep, Gibco/BRL), and osteogenic supplements (100 nM dexamethasone, 10 mM beta-glycerophosphate (Sigma-Aldrich), 0.05 mM ascorbic acid-2-phosphate (Wako Chemicals, Irving, Tex.). USC induced in osteogenic medium differentiated towards bone, as judged by several histochemical stains (FIG. 13D-FIG. 13F)—von Kossa for mineralized bone, alkaline phosphatase, and Alizarin Red for calcium deposition. RT-PCR confirmed induction of the osteogenic markers osteocalcin, Runx2 and alkaline phosphatase (FIG. 13I).

Figure 14:
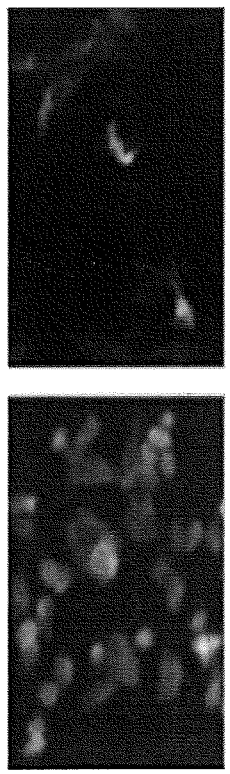
FIG. 14. Endothelial differentiation of USC. Immunofluorescence for von Willebrand's factor (vWF) (left) & CD31 (right), day 28 in endothelial cell medium-2 (EG-M™-2).

Differentiation of USC to endothelial-like cells. Endothelial induction. Cells were seeded at 3,000 cells/cm$^2$ on plastic plates precoated with 0.1% gelatin and maintain in culture for 1 month in endothelial cell medium-2 (EGM™-2, Clonetics; Cambrex Bioproducts) supplemented with 10% FBS, and Pen/Strep. Add Recombinant human bFGF (StemCell Technologies) at intervals of 2 d at 2 ng/ml. USC cultured for 4 weeks in endothelial differentiation medium were induced to express the endothelial cell markers vWF and CD 31 (FIG. 14), and levels of expression, judged by immunofluorescent staining, were comparable to those for human umbilical vessel endothelial cells.

E. Karyotype Analysis of USC

Karyotype analysis was performed to test the genetic stability of USC after serial culture (up to passage 6). At all passages of the three cell strains, analyzed karyograms showed a normal diploid (2n=38) complement of autosomes, and XY sex chromosomes (donors were male). No obvious chromosomal rearrangements could be detected by Giemsa banding of metaphase chromosomes.

EXAMPLE 7

Detection of Telomerase in USC

Figure 15:
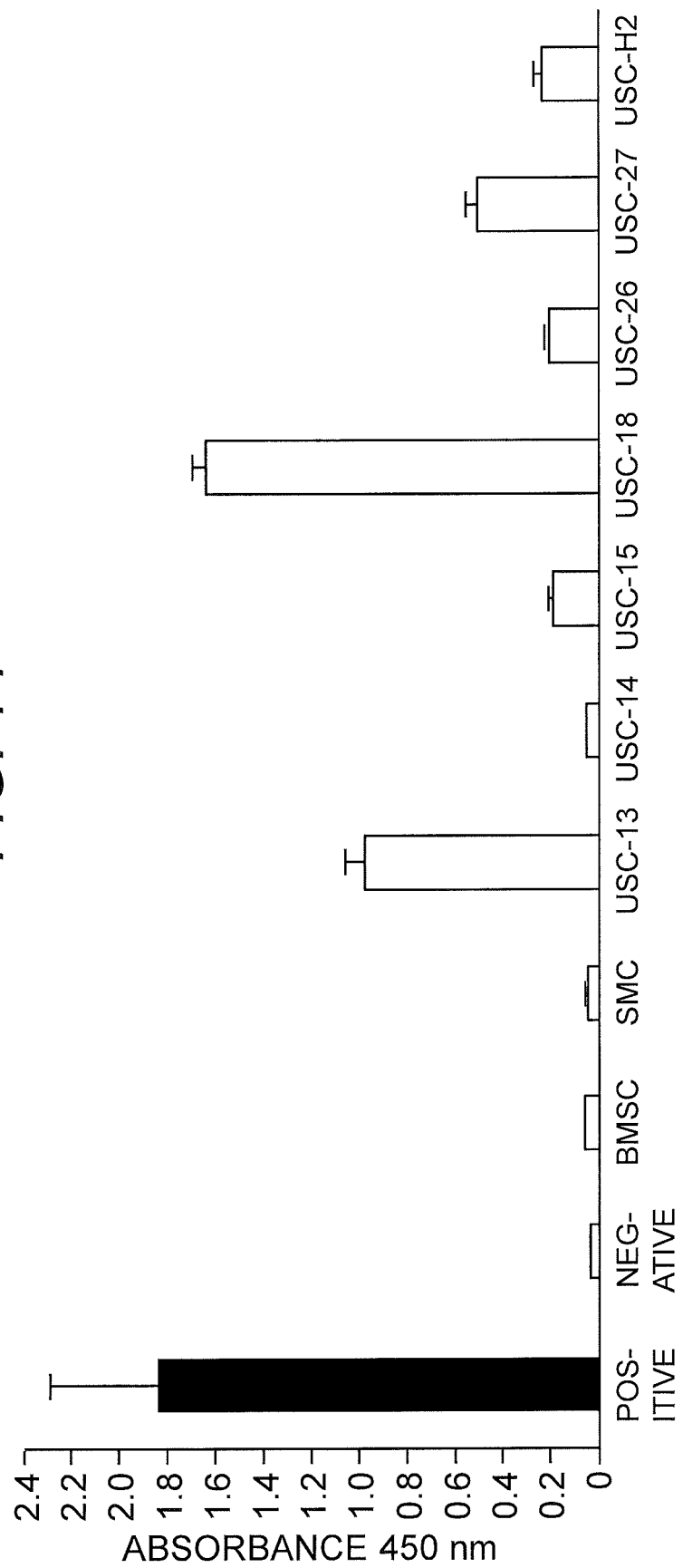
FIG. 15. Telomerase protein in USC. Lysates from $2 \times 10^4$ cells were prepared and assayed according to the manufacturers' instructions (Telo TAAGG ELISA kit, Roche). Positive (black bar)=HEK-293 cells. Negative=heat-denatured HEK-293 lysate. BMSC=human mesenchymal stromal cells from bone marrow, SMC=smooth muscle cells isolated from human bladder and USC=single clones of USC from different individuals.

The enzyme telomerase maintains telomere length in proliferating cells. It is expressed by embryonic stem cells and some adult stem cells. Our data indicates that six of seven (6/7) independent clones of USC from different individuals (ages 5 to 40 years in this set) have detectable levels of telomerase (at passages 3-6), compared to the negative control (heat-denatured lysate) (FIG. 15). By contrast, the level of telomerase protein in a commercial preparation of mesenchymal stem cells (MSC) from human bone marrow and in conventionally cultured smooth muscle cells (SMC) from human bladder were not significantly above background. Levels in two clones were similar to that in a transformed positive control cell line (HEK-293). The data are consistent with the proposed stem cell character of USC.

Long telomere length and high telomerase activity are associated with cell self-renewal and cells that can be cultured long term for many passages. The presence of telomerase suggests that USC can be maintained for a high number of population doublings.

EXAMPLE 8

Telomere Length and Telomerase Activity

A. Telomere Length

It is well known that a critical length of telomere repeat is required to ensure proper telomere function and to prevent the activation of DNA damage pathways that lead to replicative senescence and cell death. In addition, telomere length is crucial in preventing chromosomal end-to-end fusion and recombination during cell proliferation. Whenever somatic cells divide, some terminal telomere sequence is lost, so that proliferative capacity ultimately is limited both in vivo and in vitro. However, some non-embryonic stem cells and tissue-specific progenitor cells have at least a limited ability to restore telomere length and are therefore less limited in proliferative capacity. This reduced rate of telomere length loss is thought to be due to the presence of some telomerase activity in these cells.

The average telomere length of the USC is measured and compared with that of somatic cells obtained from the same individuals at the time of stem cell isolation. The rate of telomere repeat loss during cell expansion and differentiation is also measured. Human embryonal carcinoma cells (NTERA-2) are be used as a positive control for telomerase activity and long telomere length.

Telomere length can be determined by established methods. One can use the Telo TTAGGG telomere length assay kit supplied by Roche. DNA (0.5 µg) is digested with the restriction enzymes Hinf I and Rsa I and separated by electrophoresis at 80 volts in 0.8% agarose gel. Subsequently, the DNA in the gel is transferred to a "hybond" membrane (Amersham, UK) by Southern blot. Terminal restriction fragments are detected by hybridization to digoxigenin-labeled telomeric oligonucleotide following the Roche protocol. Mean telomere length can be determined using Sigma Gel Software.

B. Telomerase Activity

Telomerase is the enzyme primarily responsible for maintaining telomere length in germ cells, ES cells, and cancer stem cells and immortal cancer cells. Somatic cells have low or undetectable levels of telomerase activity, whereas post-embryonic stem cells have moderate, levels of telomerase activity which may be up-regulated when these cells differentiate into tissue-specific progenitor cells.

Telomerase activity is determined in low passage, high passage, and differentiating USC. Induced differentiation pathways tested are those of smooth muscle, urothelium, osteoblasts, chondrocytes, and endothelium.

Telomerase activity can be determined using the Telo ATGGG PCR ELISA$^{PLUS}$ kit (Roche) according to the manufacturer's protocol. Cells ($2 \times 10^5$ per sample) are lysed in 200 µl Chaps buffer, and 0.5 µg of proteinaceous supernatant will be used for PCR reaction in a total volume of 50 µl. Telomerase activity is calculated relative to the ELISA signal obtained from the control reagents supplied with the kit. A 20 µl sample of the PCR product is subjected to electrophoresis on a 12% acrylamide gel and analyzed by Southern blotting to confirm the presence of a telomerase-mediated six nucleotide DNA ladder using a Biotin Luminescent Detection kit from Roche.

If the USC originate from bladder urothelium, we would expect these cells to follow the telomerase expression pattern typically displayed by somatic stem cells. Namely, detectable levels of telomerase activity should be present during stem cell proliferation, with up-regulation of telomerase activity during early stages of differentiation into somatic tissues (progenitor cells) and a gradual loss of telomerase activity as the differentiation pathway proceeds to mature somatic cells.

To determine the relationship between ratio of expression of CD146$^+$ and high higher telomerase activity in USC, the ratio of CD146$^+$ in USC is analyzed with higher telomerase activity versus USC with low telomerase activity.

EXAMPLE 9

Markers of Perivascular Cells

Though not wishing to be bound by theory, it is hypothesized that USC may derive from perivascular cells (also called pericyte) related to MSC. Our data documents the expression of several markers of MSC/pericytes: CD146 (MCAM) by immunofluorescence and RT-PCR; NG2 (a related antigen), and PDGF-Receptorp (PDGF-Rβ) by RT-PCR (FIG. 16A-FIG. 16C). The data are consistent with the hypothesis that at least some USC are MSC-like cells that may derive from perivascular cells in the bladder. Note that, even within a clone, the expression of CD146 was not uniform at an early passage, indicating that some spontaneous differentiation may occur under present culture conditions.

EXAMPLE 10

Characterization of Smooth Muscle Cells Differentiated from USC

Urine stem cells (USC) were differentiated into smooth muscle cells (SMC) and characterized. Thirty-one urine samples were collected from 6 healthy individuals, centrifuged and re-suspended in KSFM/EFM (1:1) media. Cells were plated in 24 well dishes. Single colonies (p0) were transferred to 6 well plates (p1) and further to a 10 cm plate (p2). USC from passage 3 were used for cell differentiation studies.

No bacterial contamination was found in any of the urine samples. USC comprised an average of 10 cells/100 ml (ranging from 6 to 14 cells/100 ml). At passage-3, USC could expand to one million cells in about 3-4 weeks. Cells treated with growth factors displayed spindle-shaped architecture on 14d.

To induce UPC differentiation into SMC, cells were either treated with growth factors (TGF-β at 2.5 ng/ml and PDGF-BB at 5 ng/ml) or cultured on individual bio-matrix coatings of collagen IV (Col IV), laminin (Lam), bladder muscle cellular matrix (BMT) or acellular matrix (ECM). In addition, some USC were co-cultured with bladder SMC or in SMC-derived conditional medium.

Figure 18:
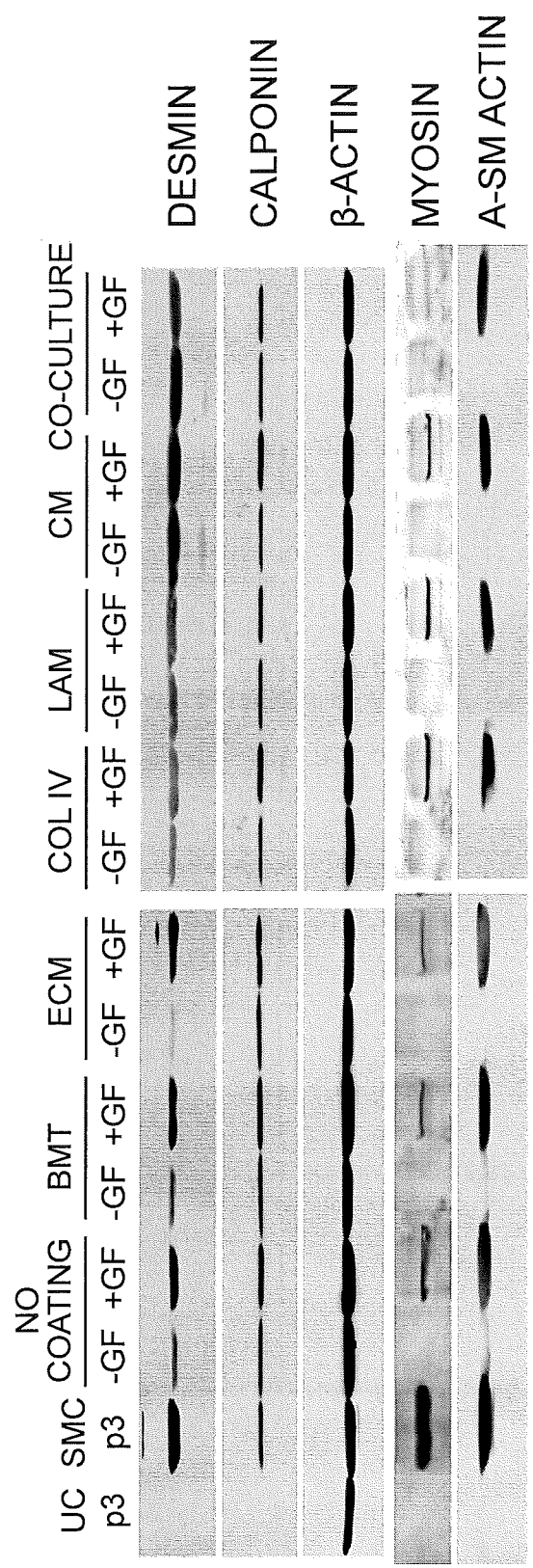
FIG. 18. Immunoblot analysis of USC treated with and without growth factors (TGF-β at 2.5 ng/ml and PDGF-BB at 5 ng/ml) and matrices for 14 days using smooth muscle-specific markers. The top panel contained 50 ug/ml protein and the bottom panel contained 100 ug/ml protein due to the weak signal of myosin.

The treated UPC were assayed for expression of SMC markers (Desmin, Myosin, Calponin) by RT-PCR, Western Blot and immunofluorescence on day 7 and 14. Bladder SMC served as a positive control and urothelial cells served as a negative control. RT-PCR performed on RNA isolated 7 and 14 days after growth factors or conditional medium addition, indicated expression of most of the transcript. However, myosin expression specifically increased only when growth factor was added (FIG. 17). Protein data correlated very well with the gene expression data with RT-PCR data (FIG. 18). The USC treated with growth factors, co-culture with SMC or SMC-conditioned media expressed smooth muscle specific proteins such as desmin and myosin. Immunofluorescence experiments also correlated with the gene and protein expression data, and expression of smooth muscle-specific proteins increased in a time-dependent manner (data not shown). Bio-matrices alone failed to induce USC to express SMC-specific transcript or proteins.

Figure 19:
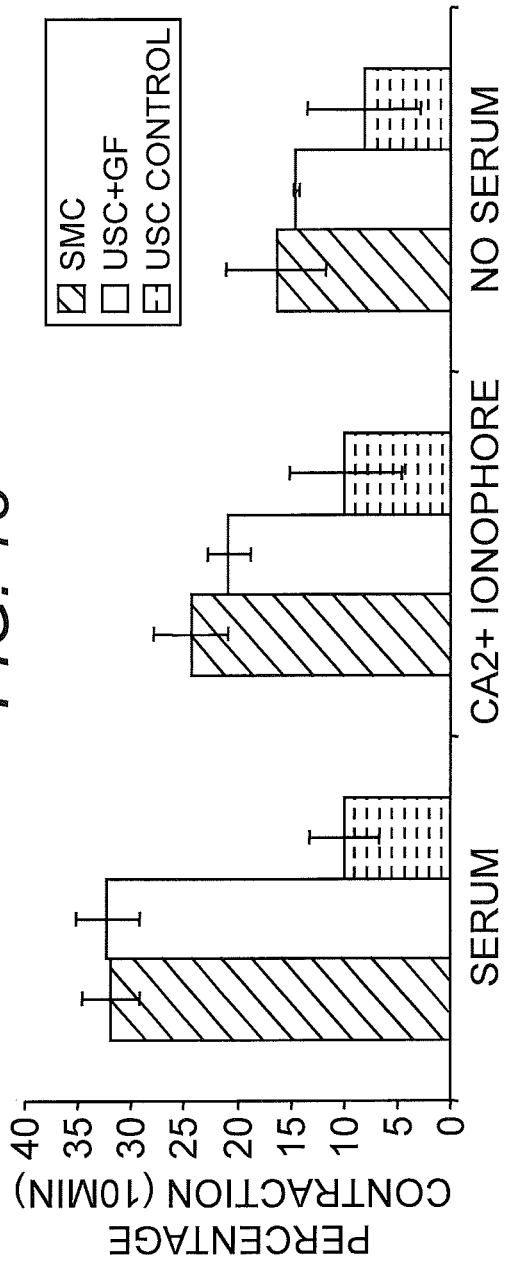
FIG. 19. Contractility after myogenic differentiation of USC. Differentiation of USC to a SMC fate was induced by growth for 7 days in culture medium with transforming growth factor-β1 (TGF-β1, 2.5 ng/ml) plus platelet-derived growth factor (PDGF-BB, 5 ng/ml). The induced USC (open bars) were compared with normal SMC isolated from human bladder (cross-hatched bars) and with undifferentiated USC (patterned bars). Cells were then placed in stabilized collagen type I lattices (1 mg/ml) and cultured for 5 days in the presence of 10% FBS (positive control), or in serum-free medium followed by stimulation with 1 µM calcium ionophore A23187 as an agonist, or in the serum-free medium without exposure to the calcium ionophore (negative control). The collagen lattice was released, and the extent of contraction exerted by the cells was determined. The mean diameter of the gel was recorded before and 10 min after release, and the percentage decrease in diameter was calculated.

Our data supports the potential of the stem cells to be induced to differentiate to functional SMC when incubated for 14 days in medium containing the myogenic growth factors (GF), i.e. TGF-β1 and PDGF-BB. One method by which to assess the functionality of SMC differentiated from USC is to determine their ability to mechanically contract lattices fabricated from collagen type I. Cell contractility of treated USC was assessed with a contractile agonist (calcium ionophore). The growth factor-treated cells were assessed for contractile function after 5 days of incubation in the collagen lattice. The extent of contraction after release of the stabilized lattice was measured, and reflects the muscle function of the cells. The data show that USC differentiated with TGF-β1 and PDGF-BB (USC+GF) were closely comparable to authentic bladder SMC in their contractile function (FIG. 19).

EXAMPLE 11

USC Seeded Bacterial Cellulose Polymer for Urinary Conduit

Porous bacterial cellulose polymer provides 3D growth of USC with multilayer of urothelium formation and cell-matrix infiltration. Bacterial cellulose (BC) polymer is a highly hydrophilic, biocompatible, non-degradable and FDA approved material with reliable mechanical properties and the stability within a wide range of temperatures and pH levels. The objective of this study is to fabricate a tissue engineered conduit with cell seeded bacterial cellulose construct for urinary reconstruction and diversion in the treatment of patients with this end-stage bladder diseases.

Porous bacterial cellulose matrixes were prepared by adding sterile paraffin particles of different size ranges: 90-150 μm, 150-300 μm and 300-500 μm, into the tubular fermentation vessel of *Acetobacter xylinum*. Human urine derived stem cells (USC) collected from the upper urinary tract were induced to differentiate into urothelium and smooth muscle cells (SMC) with epidermal and myogenic growth factors (TGF-β and PDGF), respectively. Human ureter urothelium and SMC were used as control. Ureter urothelium and SMC were seeded on BC polymer with co-culture (Group 1) or mono-(Group 2) fashions. Non-induced USC (Group 3) or co-culture of induced urothelium derived from USC (UC-USC) and SMC derived from USC (SMC-USC) were seeded on the matrix (Group 4) at $10^6$ cells/cm$^2$ at static and in 3D dynamic culture at 10 or 40 RPM up to 14 days. Cell-Seeded BC polymers were implanted in an athymic mouse model for one month. The implanted cells were tracked on cell-seeded BC grafts by using immunohistochemical labeling for human nuclear antigen.

The USC grew on the BC matrix surface, and infiltrated the matrix to larger extent when grown at 10 rpm on day 14. Urothelium-USC formed multilayers, and more SMC-USC infiltrated into BC matrix in layered co-culture (Group 4) compared to those in mono culture of urothelium-USC (Group 3). The same outcomes were seen on co-culture of ureter urothelium and SMC (Group 1) vs. culture of the urothelium alone (Group 2). No differences in cell growth and matrix infiltration among three BC matrixes with different pore sizes. Urothelium-USC lined on the BC matrix expressed urothelium markers (uroplakin I and AE1/AE3) and SMC-USC expressed SMC markers (α-smooth muscle actin and desmin) in Group 4 seven days after culture in vitro. Cell-free BC matrixes were attached with fine fibrous tissue and did not provoke inflammatory reaction in vivo. The human implanted USC were found in the grafts, and maintained urothelial and SMC phenotypes in vivo for one month.

EXAMPLE 12

Treatment of SUI and VUR with Urine Stem Cells

Examples described above demonstrate that USC possess progenitor/stem cell characteristics and can differentiate into mesoderm cell lineages such as adipocyte, osteocyte, chondrocyte, smooth muscle cells, interstitial cells and other cell types. We assessed whether human urine-derived stem cells (USC) can be used as a potential cell source for cell therapy in regenerative repair of muscular tissue defect for the treatment of stress urinary incontinence (SUI) and vesicoureteral reflux (VUR).

Twenty urine samples were collected from 9 healthy individuals. USC were isolated and expanded in vitro. Cells were identified with pericyte/mesenchymal stem cell markers. Urine derived cells ($5 \times 10^5$ cells, p3) were mixed with 0.5 ml of collagen type I (3 mg/ml) and injected subcutaneously into athymic mouse model. Implants of smooth muscle cells (SMC) mixed with collagen I were used as positive control and the cell-free collagen gel as negative control. The implants were retrieved and analyzed by histology and immunocytochemistry 14 days after injection.

No bacterial contamination was found in any of the urine samples. About 4 single urine derived cells/100 ml (ranging from 2 to 6 cells/100 ml) were found. Each single cell could expand to one million cells at passage 3 in about 3-4 weeks. Cells were positive for pericyte/mesenchymal stem cells markers (CD146, CD44, CD73, CD90, CD105, SSEA-4) and negative for hematopoietic stem cell markers (CD34, CD31 and CD45). USC presented high telomerase activity in 6 of 7 individual urine samples.

Sizes of cells-collagen implants were significantly larger than that of cell-free collagen implants, but no different in implant sizes between USC-collagen and SMC-collagen implants. Cells expressed smooth muscle markers α-smooth muscle actin and desmin in USC-collagen and SMC-collagen implants, but not in cell-free collagen implants.

Results of different treatment groups are presented in Table 5 below.

TABLE 5

| Coll Gel | Graft Weight | Cell Number | Smooth muscle cells | Interstitial Cells | New Vessels | New Nerve Fibro |
|---|---|---|---|---|---|---|
| Cell-free | + | + | − | − | − | − |
| USC | + | ++ | + | + | − | − |
| USC-VEGF | +++ | +++ | ++ | ++ | + | + |
| USC-VEGF + EC | +++ | ++++ | ++++ | ++ | ++++ | ++++ |
| USC + EC | + | ++ | ++ | + | + | + |
| USC + Coll-VEGF | + | ++ | ++ | + | + | + |
| USC + EC + Coll-VEGF | + | ++ | ++ | + | ++ | ++ |

When USC were transfected with a VEFG gene (VEGF-USC), and human umbilical vein endothelial cells (HUCEC) mixed with collagen type I gel, the number of transfected cells significantly increased compared to the non-transfected cells. More cells were positive for desmin expression. Rich capillary formation was observed and innervations with nerve fiber formation within the graft with VEFG-USC plus HUCEC-collagen I gel.

This study demonstrated that human USC can be isolated for cell expansion by a simple, safe, noninvasive and low-cost procedure. These cells expressed pericyte/mesenchymal stem cells markers and can differentiate into muscle lineages in vivo. Autoglous USC might be alternative cell source for cell-based therapy for SUI and VUR.

The foregoing is illustrative of the present invention, and is not to be construed as limiting thereof. The invention is defined by the following claims, with equivalents of the claimed to be included therein.

That which is claimed is:

1. A method for producing a culture of differentiated cells, the method comprising:
   isolating urine stem cells from a urine sample; and then
   differentiating said urine stem cells by culturing the cells in a medium that promotes said differentiating, wherein said medium that promotes said differentiating is osteogenic differentiation medium, and wherein said differentiating is osteogenic;
   to produce said culture of differentiated cells.

2. The method of claim 1, wherein said culture of differentiated cells comprises mineralized bone, calcium deposition, osteocalcin, Runx2, alkaline phosphatase, or a combination thereof after 28 days of said culturing.

3. The method of claim 1, wherein said urine stem cells are human or mammalian cells.

4. The method of claim 1, further comprising isolating a differentiated cell from the culture.

5. The method of claim 1, wherein said urine stem cells are c-kit positive, and wherein said urine stem cells can differentiate into two or more lineages selected from the group consisting of: bone, cartilage, fat, endothelium, nerve and muscle.

6. The method of claim 5, wherein said urine stem cells are positive for a marker selected from: CD133, SSEA-A, CD90, CD73, CD105, pericyte CD146 (MCAM), NG2, PDGF-Receptorβ (PDGF-Rβ), and combinations thereof, and wherein said urine stem cells are negative for a marker selected from CD31, CD34, CD45, and combinations thereof.

7. The method of claim 5, wherein said urine stem cells express telomerase.

8. The method of claim 1, further comprising seeding said differentiated cells onto a biocompatible tissue scaffold.

9. The method of claim 8, wherein said tissue scaffold comprises a collagen matrix.

10. The method of claim 8, wherein said tissue scaffold comprises a synthetic polymer.

11. The method of claim 8, wherein said tissue scaffold comprises a synthetic polymer selected from the group consisting of: polyglycolic acid (PGA), polylactic acid (PLA), and polylactic-co-glycolic acid (PLGA).

12. The method of claim 1, wherein said differentiating is carried out on a biocompatible tissue scaffold.

13. The method of claim 12, wherein said biocompatible tissue scaffold comprises a collagen matrix.

14. The method of claim 12, wherein said biocompatible tissue scaffold comprises a synthetic polymer.

15. The method of claim 12, wherein said biocompatible tissue scaffold comprises a synthetic polymer selected from the group consisting of: polyglycolic acid (PGA), polylactic acid (PLA) and polylactic-co-glycolic acid (PLGA).

16. A method for producing a culture of differentiated cells, the method comprising:
   isolating urine stem cells from a urine sample; and then
   differentiating said urine stem cells by culturing the cells in a medium that promotes said differentiating, wherein said culture of differentiated cells are smooth muscle cells that express actin, desmin, calponin, myosin, or a combination thereof.

17. The method of claim 16, wherein said method produces cultured smooth muscle tissue.

18. The method of claim 17, wherein said tissue is characterized by a contractile response to calcium ionophore in vitro.

* * * * *

UNITED STATES PATENT AND TRADEMARK OFFICE
CERTIFICATE OF CORRECTION

| | |
|---|---|
| PATENT NO. | : 11,135,248 B2 |
| APPLICATION NO. | : 15/829488 |
| DATED | : October 5, 2021 |
| INVENTOR(S) | : Zhang et al. |

It is certified that error appears in the above-identified patent and that said Letters Patent is hereby corrected as shown below:

In the Specification

Column 16, Line 25: Please correct "100 nm" to read -- 100 μm --

Column 28, Line 51: Please correct "PDGF-Receptorp" to read -- PDGF-Receptorβ --

Column 31, Line 30: Please correct "VEFG" to read -- VEGF --

Column 31, Line 36: Please correct "VEFG" to read -- VEGF --

Signed and Sealed this
Fifteenth Day of March, 2022

Drew Hirshfeld
*Performing the Functions and Duties of the*
*Under Secretary of Commerce for Intellectual Property and*
*Director of the United States Patent and Trademark Office*